(12) United States Patent
Mantovani

(10) Patent No.: US 7,041,648 B2
(45) Date of Patent: May 9, 2006

(54) COMPOSITIONS AND METHODS FOR TREATING FEMALE FERTILITY

(75) Inventor: Alberto Mantovani, Milan (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 0 days.

(21) Appl. No.: 10/785,427

(22) Filed: Feb. 25, 2004

(65) Prior Publication Data

US 2005/0152876 A1    Jul. 14, 2005

Related U.S. Application Data

(63) Continuation-in-part of application No. 10/485,640, filed as application No. PCT/IT02/00473 on Jul. 18, 2002, now abandoned.

(60) Provisional application No. 60/309,472, filed on Aug. 3, 2001.

(51) Int. Cl.
*A61K 38/00* (2006.01)

(52) U.S. Cl. .......................... 514/12; 510/350; 435/7.1

(58) Field of Classification Search ................ 514/12; 530/350; 435/7.1
See application file for complete search history.

(56) References Cited

FOREIGN PATENT DOCUMENTS

WO    99/32516 A    7/1999

OTHER PUBLICATIONS

Varani Simona et al,; "Knockout of Pentraxin 3, a Downstream Target of Growth Differentiation Factor-9, Causes Female Subfertility"; Molecular Endocrinology, vol. 16, No. 6, Jun. 2002, pp. 1154-1167, XP009002022.

*Primary Examiner*—Jon Weber
*Assistant Examiner*—Robert B. Mondesi
(74) *Attorney, Agent, or Firm*—Nixon & Vanderhye P.C.

(57) ABSTRACT

The PTX3 gene or equivalent PTX3 activity is required for female fertility. Manipulation of PTX3 activity will regulate female fertility. The effects of female sterility may be ameliorated, reproductive ability may be increased or decreased as desired, female fertility may be enhanced, or combinations thereof. The need for therapies that affect female fertility is thereby addressed.

2 Claims, 2 Drawing Sheets

SEQUENCE LISTING

```
<160> NUMBER OF SEQ ID NOS: 11

<210> SEQ ID NO 1
<211> LENGTH: 1837
<212> TYPE: DNA
<213> ORGANISM: Homo sapiens
<300> PUBLICATION INFORMATION:
<301> AUTHORS: Breviario et al.
<302> TITLE: Interleukin-1 Inducible Genes in Endothelial Cells
<303> JOURNAL: Journal of Biological Chemistry
<304> VOLUME: 267
<305> ISSUE: 31
```

<306> PAGES: 22190-22197
<307> DATE: 1992-11-05
<308> DATABASE ACCESSION NUMBER: X636613
<309> DATABASE ENTRY DATE: 1993-07-29

<400> SEQUENCE: 1

```
ctcaaactca gctcacttga gagtctcctc ccgccagctg tggaaagaac tttgcgtctc      60
tccagcaatg catctccttg cgattctgtt ttgtgctctc tggtctgcag tgttggccga     120
gaactcggat gattatgatc tcatgtatgt gaatttggac aacgaaatag acaatggact     180
ccatccccact gaggacccca cgccgtgcga ctgcggtcag gagcactcgg aatgggacaa    240
gctcttcatc atgctggaga actcgcagat gagagagcgc atgctgctgc aagccacgga     300
cgacgtcctg cggggcgagc tgcagaggct gcgggaggag ctgggccggc tcgcggaaag     360
cctggcgagg ccgtgcgcgc cggggctcc cgcagaggcc aggctgacca gtgctctgga      420
cgagctgctg caggcgaccc gcgacgcggg ccgcaggctg gcgcgtatgg agggcgcgga     480
ggcgcagcgc ccagaggagg cggggcgcgc cctggccgcg gtgctagagg agctgcggca     540
gacgcgagcc gacctgcacg cggtgcaggg ctgggctgcc cggagctggc tgccggcagg     600
ttgtgaaaca gctatttttat tcccaatgcg ttccaagaag attttttggaa gcgtgcatcc    660
agtgagacca atgaggcttg agtcttttag tgcctgcatt tgggtcaaag ccacagatgt      720
attaaacaaa accatcctgt tttcctatgg cacaaagagg aatccatatg aaatccagct     780
gtatctcagc taccaatcca tagtgtttgt ggtgggtgga gaggagaaca aactggttgc      840
tgaagccatg gtttccctgg aaggtggac ccacctgtgc ggcacctgga attcagagga      900
agggctcaca tccttgtggg taaatggtga actggcggct accactgttg agatggccac      960
aggtcacatt gttcctgagg gaggaatcct gcagattggc caagaaaaga atggctgctg    1020
tgtgggtggt ggctttgatg aaacattagc cttctctggg agactcacag gcttcaatat    1080
ctgggatagt gttcttagca atgaagagat aagagagacc ggaggagcag agtcttgtca    1140
catccggggg aatattgttg ggtggggagt cacagagatc cagccacatg gaggagctca    1200
gtatgtttca taaatgttgt gaaactccac ttgaagccaa agaaagaaac tcacacttaa    1260
aacacatgcc agttgggaag gtctgaaaac tcagtgcata taggaacac ttgagactaa     1320
tgaaagagag agttgagacc aatctttatt tgtactggcc aaatactgaa taaacagttg    1380
aaggaaagac attggaaaaa gcttttgagg ataatgttac tagactttat gccatggtgc    1440
tttcagttta atgctgtgtc tctgtcagat aaactctcaa ataattaaaa aggactgtat    1500
tgttgaacag agggacaatt gttttacttt tctttggtta attttgtttt ggccagagat    1560
gaattttaca ttggaagaat aacaaaataa gatttgttgt ccattgttca ttgttattgg    1620
tatgtacctt attacaaaaa aaatgatgaa acatattta tactacaagg tgacttaaca     1680
actataaatg tagtttatgt gttataatcg aatgtcacgt ttttgagaag atagtcatat    1740
aagttatatt gcaaaaggga tttgtattaa tttaagacta tttttgtaaa gctctactgt    1800
aaataaaata tttttataaaa ctaaaaaaaa aaaaaa                              1837
```

<210> SEQ ID NO 2
<211> LENGTH: 381
<212> TYPE: PRT
<213> ORGANISM: Homo sapiens
<220> FEATURE:
<221> NAME/KEY: SIGNAL PEPTIDE
<222> LOCATION: (1)..(17)
<223> OTHER INFORMATION:
<220> FEATURE:

```
<221> NAME/KEY: MAT_PEPTIDE
<222> LOCATION: (18)..(381)
<300> PUBLICATION INFORMATION:
<301> AUTHORS: Breviario et al.
<302> TITLE: Interleukin-1 Inducible Genes in Endothelial Cells
<303> JOURNAL: Journal of Biological Chemistry
<304> VOLUME: 267
<305> ISSUE: 31
<306> PAGES: 22190-22197
<307> DATE: 1992-11-05
<308> DATABASE ACCESSION NUMBER: CAA45158
<309> DATABASE ENTRY DATE: 1993-07-29

<400> SEQUENCE: 2

Met His Leu Leu Ala Ile Leu Phe Cys Ala Leu Trp Ser Ala Val Leu
        -15                 -10                  -5

Ala Glu Asn Ser Asp Asp Tyr Asp Leu Met Tyr Val Asn Leu Asp Asn
 -1   1              5                  10                  15

Glu Ile Asp Asn Gly Leu His Pro Thr Glu Asp Pro Thr Pro Cys Asp
                 20              25              30

Cys Gly Gln Glu His Ser Glu Trp Asp Lys Leu Phe Ile Met Leu Glu
             35              40              45

Asn Ser Gln Met Arg Glu Arg Met Leu Leu Gln Ala Thr Asp Asp Val
         50              55              60

Leu Arg Gly Glu Leu Gln Arg Leu Arg Glu Glu Leu Gly Arg Leu Ala
 65              70              75

Glu Ser Leu Ala Arg Pro Cys Ala Pro Gly Ala Pro Ala Glu Ala Arg
 80              85              90              95

Leu Thr Ser Ala Leu Asp Glu Leu Leu Gln Ala Thr Arg Asp Ala Gly
             100             105             110

Arg Arg Leu Ala Arg Met Glu Gly Ala Glu Ala Gln Arg Pro Glu Glu
             115             120             125

Ala Gly Arg Ala Leu Ala Ala Val Leu Glu Glu Leu Arg Gln Thr Arg
             130             135             140

Ala Asp Leu His Ala Val Gln Gly Trp Ala Ala Arg Ser Trp Leu Pro
 145             150             155

Ala Gly Cys Glu Thr Ala Ile Leu Phe Pro Met Arg Ser Lys Lys Ile
 160             165             170             175

Phe Gly Ser Val His Pro Val Arg Pro Met Arg Leu Glu Ser Phe Ser
             180             185             190

Ala Cys Ile Trp Val Lys Ala Thr Asp Val Leu Asn Lys Thr Ile Leu
             195             200             205

Phe Ser Tyr Gly Thr Lys Arg Asn Pro Tyr Glu Ile Gln Leu Tyr Leu
             210             215             220

Ser Tyr Gln Ser Ile Val Phe Val Val Gly Gly Glu Glu Asn Lys Leu
 225             230             235

Val Ala Glu Ala Met Val Ser Leu Gly Arg Trp Thr His Leu Cys Gly
 240             245             250             255

Thr Trp Asn Ser Glu Glu Gly Leu Thr Ser Leu Trp Val Asn Gly Glu
             260             265             270

Leu Ala Ala Thr Thr Val Glu Met Ala Thr Gly His Ile Val Pro Glu
             275             280             285

Gly Gly Ile Leu Gln Ile Gly Gln Glu Lys Asn Gly Cys Cys Val Gly
             290             295             300

Gly Gly Phe Asp Glu Thr Leu Ala Phe Ser Gly Arg Leu Thr Gly Phe
 305             310             315

Asn Ile Trp Asp Ser Val Leu Ser Asn Glu Glu Ile Arg Glu Thr Gly
```

```
            320                 325                 330                 335
Gly Ala Glu Ser Cys His Ile Arg Gly Asn Ile Val Gly Trp Gly Val
                340                 345                 350
Thr Glu Ile Gln Pro His Gly Gly Ala Gln Tyr Val Ser
            355                 360

<210> SEQ ID NO 3
<211> LENGTH: 1841
<212> TYPE: DNA
<213> ORGANISM: Mus musculus
<300> PUBLICATION INFORMATION:
<301> AUTHORS: Introna et al.
<302> TITLE: Cloning of Mouse PTX3
<303> JOURNAL: Blood
<304> VOLUME: 87
<305> ISSUE: 5
<306> PAGES: 1862-1872
<307> DATE: 1996-03-01
<308> DATABASE ACCESSION NUMBER: X83601
<309> DATABASE ENTRY DATE: 1996-01-10

<400> SEQUENCE: 3
actcctgcct cacactatct ctcccgggct caaactcgga tcactgtaga gtctcgcttc      60
ttcccctgcg gctgcgaacg aaatttcgcc tctccagcaa tgcacctccc tgcgatcctg     120
ctttgtgctc tctggtctgc agtagtggct gagacctcgg atgactacga gctcatgtat     180
gtgaatttgg acaacgaaat agacaatgga cttcatccca ccgaggaccc cacgccatgc     240
gactgccgcc aggagcactc ggagtgggac aagctgttca tcatgctgga gaactcgcag     300
atgcgggagg gcatgctgtt gcaggccacc gacgacgtcc tccgtggaga gctgcagcgg     360
ctgcgggcag agctggggcg gctggcgggc ggcatggcga ggccgtgcgc agccggtggc     420
cccgcagacg ccaggctggt gcgggcgctg gagccgctgc tgcaggagag ccgtgacgcg     480
agcctcaggc tggcgcgcct ggaggacgcg gaggcgcggc gacccgaggc gacagtgcct     540
ggcctaggcg ctgtgctgga ggaactgcgg cggacgcgcg ccgacctgag cgccgtgcag     600
agctgggtcg cccgccactg gctgcccgca ggttgtgaaa cagcaatttt cttcccaatg     660
cgttcgaaga agatttttgg aagcgtgcat cctgtgagac caatgaagct tgaatctttt     720
agtacttgca tttgggtcaa agccacagat gtattaaaca aaaccatcct gttttcttat     780
ggcacaaagt ggaaccccta tgagattcag ctgtacctca gttcccagtc cctagtgttg     840
gtggtgggtg gaaaggagaa caagctggct gcagacactg tggtgtccct ggggaggtgg     900
tcccacctgt gtggcacctg gagttcagag caggggagca tgtccctgtg gcaaacggg      960 gagctggtgg ctaccactgt agagatggcc aaaagtcact ctgttcctga gggtggactc    1020
ctacagattg gccaagaaaa gaatggttgc tgtgtaggtg ggggctttga cgaatcatta    1080
gcattttctg gaagaatcac aggcttcaat atctgggatc gggttctcag cgaggaggag    1140
atacgggcca gtgaggagt cgaatcctgt cacatccggg gaaatgtcgt cggtggggga    1200
gtcacagaga ttcaggcgca cggaggagcc cagtatgttt cttaagtgtt gtgaaaatct    1260
acttgaagcc aaaggagact cacattttaa atatgccagt tggaaaagtc tgaaaacttc    1320
ggtgcgtaat agacgaatga aggagagact tgagattgtc tttgtttatc ttggcaaaat    1380
actgaataca cagttgaagg gaaggcttga gagagggctc cgggatgttg ttactaagcc    1440
ttatactgtg gtgctttcag attaatgtct gcctctgtca gataaaccct cagataacta    1500
aacatgactg gactctgaac agagggacga ttgtgtgact tttttttttt ttattttgg    1560 ttaattttat tttggccaga gacatttta tattggaaga ataacaaaac aagctctgtt    1620
```

```
gcccattgtt cattctttct ggtgtgtatt ttgtgacaaa agagatgatg agaaaaccat    1680
aattatacca caaagtgact tattaacgaa cataaatgta gcttacgtgt tataatccaa    1740
tccatttggg agaaggtagt tgtgtaattt atattgtgaa atgtaattgt attaatttta    1800
tttttgtaaa agtctactgt aaataaattg ttttataaag c                       1841
```

<210> SEQ ID NO 4
<211> LENGTH: 381
<212> TYPE: PRT
<213> ORGANISM: Mus musculus
<220> FEATURE:
<221> NAME/KEY: SIGNAL PEPTIDE
<222> LOCATION: (1)..(17)
<223> OTHER INFORMATION:
<220> FEATURE:
<221> NAME/KEY: MAT_PEPTIDE
<222> LOCATION: (18)..(381)
<223> OTHER INFORMATION:
<300> PUBLICATION INFORMATION:
<301> AUTHORS: Introna et al.
<302> TITLE: Cloning of Mouse PTX3
<303> JOURNAL: Blood
<304> VOLUME: 87
<305> ISSUE: 5
<306> PAGES: 1862-1872
<307> DATE: 1996-03-01
<308> DATABASE ACCESSION NUMBER: CAA58580
<309> DATABASE ENTRY DATE: 1996-01-10

<400> SEQUENCE: 4

```
Met His Leu Pro Ala Ile Leu Leu Cys Ala Leu Trp Ser Ala Val Val
        -15                 -10                  -5

Ala Glu Thr Ser Asp Asp Tyr Glu Leu Met Tyr Val Asn Leu Asp Asn
-1   1               5                  10                  15

Glu Ile Asp Asn Gly Leu His Pro Thr Glu Asp Pro Thr Pro Cys Asp
                20                  25                  30

Cys Arg Gln Glu His Ser Glu Trp Asp Lys Leu Phe Ile Met Leu Glu
            35                  40                  45

Asn Ser Gln Met Arg Glu Gly Met Leu Leu Gln Ala Thr Asp Asp Val
        50                  55                  60

Leu Arg Gly Glu Leu Gln Arg Leu Arg Ala Glu Leu Gly Arg Leu Ala
    65                  70                  75

Gly Gly Met Ala Arg Pro Cys Ala Ala Gly Gly Pro Ala Asp Ala Arg
80                  85                  90                  95

Leu Val Arg Ala Leu Glu Pro Leu Leu Gln Ser Arg Asp Ala Ser
                100                 105                 110

Leu Arg Leu Ala Arg Leu Glu Asp Ala Glu Ala Arg Arg Pro Glu Ala
            115                 120                 125

Thr Val Pro Gly Leu Gly Ala Val Leu Glu Glu Leu Arg Arg Thr Arg
        130                 135                 140

Ala Asp Leu Ser Ala Val Gln Ser Trp Val Ala Arg His Trp Leu Pro
    145                 150                 155

Ala Gly Cys Glu Thr Ala Ile Phe Phe Pro Met Arg Ser Lys Lys Ile
160                 165                 170                 175

Phe Gly Ser Val His Pro Val Arg Pro Met Lys Leu Glu Ser Phe Ser
                180                 185                 190

Thr Cys Ile Trp Val Lys Ala Thr Asp Val Leu Asn Lys Thr Ile Leu
            195                 200                 205

Phe Ser Tyr Gly Thr Lys Trp Asn Pro Tyr Glu Ile Gln Leu Tyr Leu
        210                 215                 220
```

```
Ser Ser Gln Ser Leu Val Leu Val Val Gly Gly Lys Glu Asn Lys Leu
    225                 230                 235
Ala Ala Asp Thr Val Val Ser Leu Gly Arg Trp Ser His Leu Cys Gly
240                 245                 250                 255
Thr Trp Ser Ser Glu Gln Gly Ser Met Ser Leu Trp Ala Asn Gly Glu
                260                 265                 270
Leu Val Ala Thr Thr Val Glu Met Ala Lys Ser His Ser Val Pro Glu
                275                 280                 285
Gly Gly Leu Leu Gln Ile Gly Gln Glu Lys Asn Gly Cys Cys Val Gly
                290                 295                 300
Gly Gly Phe Asp Glu Ser Leu Ala Phe Ser Gly Arg Ile Thr Gly Phe
                305                 310                 315
Asn Ile Trp Asp Arg Val Leu Ser Glu Glu Ile Arg Ala Ser Gly
320                 325                 330                 335
Gly Val Glu Ser Cys His Ile Arg Gly Asn Val Val Gly Trp Gly Val
                340                 345                 350
Thr Glu Ile Gln Ala His Gly Gly Ala Gln Tyr Val Ser
                355                 360
```

<210> SEQ ID NO 5
<211> LENGTH: 1531
<212> TYPE: DNA
<213> ORGANISM: Homo sapiens
<220> FEATURE:
<221> NAME/KEY: PROMOTER
<222> LOCATION: (1)..(1317)
<223> OTHER INFORMATION:
<220> FEATURE:
<221> NAME/KEY: PROTEIN_BIND
<222> LOCATION: (1222)..(1231)
<223> OTHER INFORMATION: NF-kB
<300> PUBLICATION INFORMATION:
<301> AUTHORS: Basile et al.
<302> TITLE: Characterization of the Promoter for the Human Long
      Pentaxin PTX3
<303> JOURNAL: Journal of Biological Chemistry
<304> VOLUME: 272
<305> ISSUE: 13
<306> PAGES: 8172-8178
<307> DATE: 1997-03-28
<308> DATABASE ACCESSION NUMBER: X97748
<309> DATABASE ENTRY DATE: 1997-11-15

<400> SEQUENCE: 5

```
gaattcccg gatctcccctt ctaactctcc acctttggcc taagctttgc ttccacatgg      60
tcatcaacat ttggtggtta tagaactaat aaccccctatc tcacttcact cctatgccag     120
agggccccta gcatcagctc atgggattgt tgttttttgct ttcctctcta tctttggctc    180
cgggattttc cccttacttt aatgggagct catctgtacc ttttaagttt ttattaatat     240
catgtgaaca cagacctgta tatattgtta gaagcagaaa tctctaagtt tactttttaaa    300
acatgatcct tgcctcgaaa ccttgtagaa taatataatg tccacataat accaagttat     360
gaaaagaaac atacctaaat aactaaataa gtatattcct ttttttcccccc agctttttttt 420
ccccattcta ggttacccag ttgtactgtg ttgtttgtca taggccgggt gaggtggctc     480
acgtctgtaa tcctagcaat ttgggaggcg aaggcgggtg gatcgcctga ggtcaggagt     540
tcgagaccag cctggctaac atggtgaaac cctgtctcta ctaaaaatac aaaaattaac     600
tgggtgtggt ggcgggtgcc tgtaattcca gctactggg aagctgaggt aggagaatcg      660
cttgaaccca ggatgcggag gttgcagtga gccgagatca caccattgca ctccagcctg    720
```

```
ggcaacaaga gcgaaattca gtctcaaaaa aaaaaattat ctataaaagt ataggtgcaa      780
ctcctcaagt attaaagaca agatagctcg gattggactt gactttcaga gccataacta      840
ttcttaatat gttggtttat cttggaatca gaccattttc agtttcaacc tgtaaaacag      900
tgtacaaagg aaacatggaa agttttctat atataaaggg ttgtgaaata ataacagctc      960
acagaaaatg ctgaaatgat gatttgcttc agtaccctct gaaatttctc ccctaccacc     1020
cctccttcat ccccattgct atcaattcaa attacaacag ctaattctca ggagaacagt     1080
agaagcccag tttctctcct ctttcccctc tgaccctcct ccaattaatc tgactgcagc     1140
gtaaaccttt gcggtttaat attgtgcaac ttccacattt ccctcgctct cccacccagc     1200
cccctccccc accaaattca ggggaactcc cgttaccgca gtgccaccag cattactcat     1260
tcatccccat tcaggctttc ctcagcattt attaaggact ctctgctcca gcctctcact     1320
ctcactctcc tccgctcaaa ctcagctcac ttgagagtct cctcccgcca gctgtggaaa     1380
gaactttgcg tctctccagc aatgcatctc cttgcgattc tgttttgtgc tctctggtct     1440
gcagtgttgg ccgagaactc ggatcattat catctcatgt atgtgaattt ggacaacgaa     1500
atagacaatg gactccatcc cactgaggac c                                    1531
```

<210> SEQ ID NO 6
<211> LENGTH: 2708
<212> TYPE: DNA
<213> ORGANISM: Mus musculus
<220> FEATURE:
<221> NAME/KEY: PROMOTER
<222> LOCATION: (1)..(1373)
<223> OTHER INFORMATION:
<300> PUBLICATION INFORMATION:
<301> AUTHORS: Altmeyer et al.
<302> TITLE: Promoter Structure and Transcriptional Activation . . .
<303> JOURNAL: Journal of Biological Chemistry
<304> VOLUME: 270
<305> ISSUE: 43
<306> PAGES: 25584-15590
<307> DATE: 1995-10-27
<308> DATABASE ACCESSION NUMBER: U33842
<309> DATABASE ENTRY DATE: 1995-10-27

<400> SEQUENCE: 6

```
atcccagagg ctctctgtac tggcattagg acctcacagc accacatcag gtttcttaat       60
gtggactcta gaaactgaac tcgagcccac agccttagga gaaaagcacc ttacaaagct      120
gtggctccac actgcccttt aaacaatatc gtattgtctc atattgccat cgctttctga      180
tggctttaac ggtttcaaac ataccctgtc tttagccgtg atctcaaata agtgaagctc      240
ttgagcaggg gcctgatgcc ttttgacttt gtgttgattc atgcttatga tgccctgttc      300
cctccgtgtc tagctatgtt taactgtgga ttcaattttt attggtgggt ggattggtac      360
atgcatgtgc attccagatg cgtgagggca ctcaggccag gaaagccact catgagtctc      420
tgtcaggagc agaggaattt acctatggaa atccaagagc agccttctga gaggcctggc      480
ctgagggtag taccccctccc atcatgatca ggatgtgact ggtaaccctc cccctccatc      540
tcctttgtat attggagact tgtatcagct caggggtatc tctgggagt ggttccctct      600 agatctgtgt agttttttag atcttgcttt atttggagtt tattctcatg ttttaatttt      660
ttatcactat tattatgact tatcaacacc tatctaggta cttttcactg ggggagggg       720 caggttttac acacacacac acacacacac acacacacac acacacacac acagtcacta      780
atgtaaaatt taaacaggg accttgatag gatatgtcca agaatacccca agcaccctaa      840 agccactata ttcccgccct cactttcctg ttttactggg ttttgaccca gccatactgt      900
```

```
gttttttagt tgctccacca gaggagtcaa gactagttag tcaagattga cttctagagt    960
cataaaaatt cttaatgggt tattttggag tcacggaatc attttctata gcttggtctt   1020
gagaaagtat ccaaaggaaa agtgaaaaaa aaagttttc cataacttca ggggttgtgg    1080
agtaatgaaa gctcacacca aatgccaaaa tgataattcg ccctgtacct ctgtgctcct   1140
caccccccaa agcgctagca cttcaggtta cagcaactaa tcctcagggg caccagaaaa   1200
gtccagcttc cctcccttc tcccctgac tcgcctctaa ttaatctgcc tgcagtgtgg    1260
acctcggtgg tttaacattg tgcaacctct tcagctccct tgccctccca cccaaccccc   1320
tcccccaaat ccaggggaac tccctcgcgc tgtgccaccg acattagtca ttcatccgct   1380
catgctttgg agcgtttatt aagggcttca ctcctgcctc acactatctc tcccgggctc   1440
aaactcggat cactgtagag tctcgcttct tcccctgcgg gtgcgaagca aatttcggct   1500
ctccagcaat gcacctccct gcgatcctgc tttgtgctct ctggtctgca gtagtggctg   1560
agacctcgga tgactacgag ctcatgtatg tgaatttgga caacgaaata gacaatggac   1620
ttcatcccac cgaggaccgt aagttcattt ttaactctct cagcgtatca aaactacata   1680
actcacttct ggggggcgc gattaacata attaacatag atagccaatg aagcaagcta    1740
aaattatact ttatttgtga agcaaggac tgggggaaaa aaggaaagca aggaaatatc    1800
tgagaaaagc cagaggtttt aaattatttt tgtaacattt atgatgagtt aagttatacg   1860
aaatctttaa ctgtttttag ctatattaat ggcattttct cagttagttt aacatgtcta   1920
taaagaatag tctgtgtcat cttttgagttt acacgcacgc tgttttcaga gctatcctta   1980
gaaggagagc gttgctgggg acaggctgaa acttggagtc accaagagtg caacccatgg   2040
ccacccagga caagctgata acacttgtgt gtgtcctgcg ttctagccac gccatgcgac   2100
tgcgcccagg agcactcgga gtgggacaag ctgttcatca tgctggagaa ctcgcagatg   2160
cgggagggca tgctgttgca ggccaccgac gacgtcctcc gtggagagct gcagcggctg   2220
cggtcagagc tgggccggct ggcgggcggc atggcgaggc cgtgcgcagc cggtggcccc   2280
gcagacgcca ggctggtgcg ggcgctggag ccgctgctgc aggagagccg tgacgcgagc   2340
ctcaggctgg cgcgcctgga ggacgcggag gcgcggcgac ccgaggcgac agtgcctggc   2400
ctaggcgctg tgctggagga actgcggcgg acgcgctccg acctgagcgc cgtgcagagc   2460
tgggtcgccc accactggct gcccgcaggt aagcccacgg tcggctctgt ccctagaggc   2520
aagcttttgt gggaccctca cactcagagc cccagtactt tcataggca cactcacaga    2580 gctcacacca cgccaggcag ctcattgcct tttaaaagta tttccaagcc cgaggaaccc   2640
aaaagaaaaa aacgaggatt taaaccatca gtctggaagt tgacgtcaga ggttcctgat   2700
accggatc                                                            2708
```

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 7
agcaatgcac ctccctgcga t                                               21

<210> SEQ ID NO 8
<211> LENGTH: 21
<212> TYPE: DNA

```
<213> ORGANISM: Artificial Sequence
<220> FEATURE:
<223> OTHER INFORMATION: Oligonucleotide Primer

<400> SEQUENCE: 8
tcctcggtgg gatgaagtcc a                                              21

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 9
ctgctcttta ctgaaggctc                                                20

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 10
tcctcggtgg gatgaagtcc a                                              21

<210> SEQ ID NO 11
<211> LENGTH: 8
<212> TYPE: PRT
<213> ORGANISM: Artificial Sequence
<220> FEATURE:
<223> OTHER INFORMATION: Consensus "pentraxin-like" sequence
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
<222> LOCATION: (5)..(5)
<223> OTHER INFORMATION: Ser or Thr
<220> FEATURE:
<221> NAME/KEY: MISC_FEATURE
<222> LOCATION: (7)..(7)
<223> OTHER INFORMATION: any amino acid

<400> SEQUENCE: 11

His Xaa Cys Xaa Xaa Trp Xaa Ser
1               5
```

COMPOSITIONS AND METHODS FOR TREATING FEMALE FERTILITY

Figure 1:
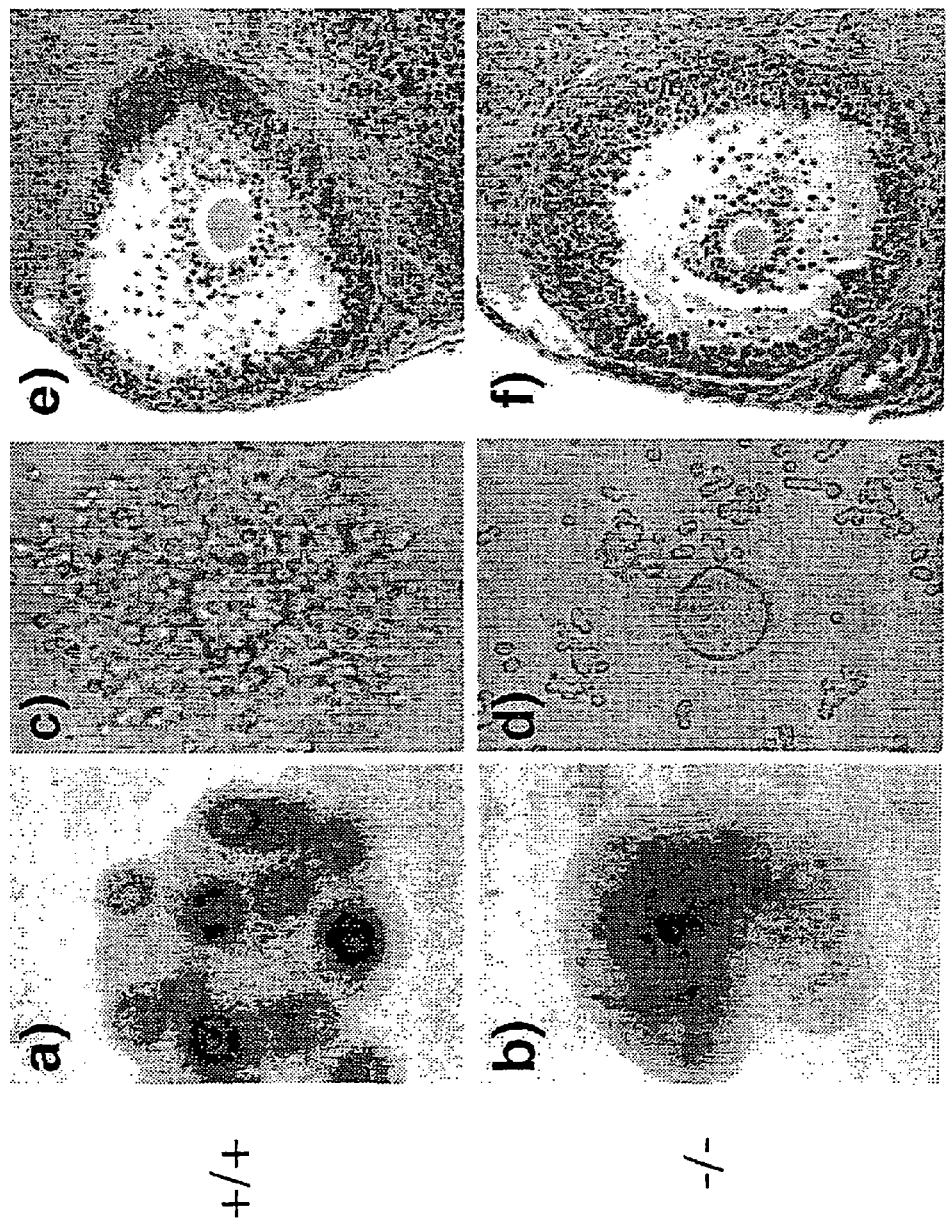

The present application is a continuation-in-part of Ser. No. 10/485,640, filed 3 Feb. 2004 now abandoned, which is a 371 U.S. national phase of International Application PCT/IT02/00473, filed 18 Jul. 2002, which designated the U.S., and claims benefit of U.S. Provisional Application Ser. No. 60/309,472, filed 3 Aug. 2001, the entire contents of each of which is hereby incorporated by reference.

This invention relates to the requirement of PTX3 activity for female fertility. The present application demonstrates that a genetic mutation which reduces PTX3 activity results in female sterility.

Pentraxins are a superfamily of proteins, which is characterized by a cyclic multimeric structure [1]. The classical short pentraxins C-reactive protein (CRP) and serum amyloid P component (SAP) are acute phase proteins in man and mouse, respectively, produced in the liver in response to inflammatory mediators; in particular, they are directly induced by interleukin-6 [2–3].

Long pentraxins share similarities with the classical short pentraxins, but differ by the presence of an unrelated long N-terminal domain coupled to the C-terminal pentraxin domain, as well by genomic organization, chromosomal localization, cellular source, inducing stimuli, and ligands recognized. Long pentraxin 3 (PTX3) is the first long pentraxin identified as an interleukin-1 (IL-1) inducible gene in endothelial cells [4] and as a tumor necrosis factor-α (TNFα)) inducible gene in fibroblasts [5]. PTX3 is also produced by macrophages and other cell types and tissues upon stimulation with primary inflammatory mediators (LPS, IL-1, TNFα) [6–8]. PTX3 consists of a C-terminal 203-amino acid pentraxin-like domain and an N-terminal 178-amino acid unrelated domain. When secreted, glycosylated PTX3 protomers (45 kDa) assemble to form 10–20 multimers [9]. PTX3 does not bind to classical pentraxin ligands such as phosphoethanolamine, phosphocholine, high pyruvate agarose, collagen IV, fibronectin, or gelatin. In contrast, PTX3 specifically binds with high affinity to C1q by the pentraxin domain [9]. PTX3 plasma levels are very low in normal conditions ($\leq 2$ ng/ml) but increase in several pathological conditions (10–100 ng/ml) including infections [10].

Other long pentraxins cloned after PTX3 include guinea pig apexin [11, 12] which is expressed in the sperm acrosome, XL-PXN1 from *Xenopus laevis* [13], rat neuronal pentraxin 1 (NP1) [14], human NP1 and NP2 [15, 16], mouse NP1 and NP2 [15], Narp [17], and neuronal pentraxin receptor (NRP), a putative integral membrane pentraxin [18-9]. The in vivo function of long pentraxins has not been unequivocally defined.

PTX3 consists of two structural domains: a N-terminal domain unrelated to any known molecule and a C-terminal domain similar to the short pentraxins such as C-reactive protein (Breviario et al., J. Biol. Chem., 267:22190–22197, 1992).

Substantial similarity has been found between human PTX3 (hPTX3) and mouse PTX3 (mPTX3). The degree of identity between human and murine PTX3 genes is 82%, and reaches 90% if conservative substitutions are considered (Introna et al., Blood, 87:1862–1872, 1996). The genes are located in syntenic chromosome locations. The high degree of similarity between hPTX3 and mPTX3 sequences is a sign of the high degree of conservation of pentraxins during evolution (Pepys & Baltz, Adv. Immunol., 34:141–212, 1983). Pentraxins are reviewed by Gewurz et al. (Curr. Opin. Immunol., 7:54–64, 1995).

WO 99/32516 describes the use of PTX3 for the therapeutic treatment of cancer, inflammation, and infectious diseases.

U.S. Pat. No. 5,767,252 describes a growth factor for neuronal cells belonging to the pentraxin family.

WO 02/36151 describes the use of PTX3 for the preparation of medicament for the prevention and treatment of autoimmune pathologies.

In contrast to the foregoing, the study of mice genetically modified at their PTX3 genetic locus, which were produced by homologous recombination in embryonic stem cells, and the effects thereof has revealed the involvement of PTX3 activity in female fertility.

It is an objective of the invention to manipulate PTX3 activity and thereby regulate female fertility. The effects of female sterility may be ameliorated, reproductive ability may be increased or decreased as desired, female fertility may be enhanced, or combinations thereof. Other treatments such as in vitro fertilization require invasive procedures and complicated technology. The need for therapies that affect female fertility is thereby addressed. Other advantages and improvements are discussed below, or would be apparent from the disclosure herein.

Pharmaceutical compositions, methods for using and making them, and further objectives are described below.

An object of the invention is to provide a pharmaceutical composition which is comprised of an agent which changes PTX3 activity in an amount sufficient to affect female reproductive ability. The discovery that PTX3 activity is required for successful oocyte fertilization may be used according to the present invention as the basis for a conraceptive method to reduce fertility of a femal patient or animal, and/or as the a basis for a therapy of a female patient or animal with a defect in reproduction, and/or for diagnosis of the ability of a female patient or animal to reproduce, and/or as the basis for a method to develop drugs or medicines or therapies which reduce or treat infertility or enhance or treat infertility. One of ordinary skill will apprecaite from the present disclosure that reduction of the activity or amount of the function of PTX3 will reduce fertility or increase infertility of a female patient or animal and enhancement or increase in the activity or amount of the function of PTX3 will increase fertility or reduce infertility relating to PTX3 deficiency of a female patient or animal. Such changes or alterations in the PTX3 levels or activity or affinities are, in one embodiment of the invention, preferably produced locally, near the cite of action of oocyte fertilization or potential oocyte fertilization.

Examples of such agents include polynucleotides corresponding to PTX3 genes or encoding PTX3, polypeptides corresponding to PTX3 proteins encoded thereby, and others that increase or decrease PTX3 gene expression. This includes the nucleotide and amino acid sequences listed herein, analogs thereof, those containing muta-tions or polymorphisms, and other variants thereof (e.g., partial-length oligo-nucleotides and oligopeptides). Antibodies and fragments thereof which may antagonize the function of PTX3 are an example of such agents.

Hybrids between at least one PTX3 portion and a heterologous portion (polynucleotide or polypeptide) are considered chimeric gene or fusion protein variants, respectively. Genetic vectors may be used to shuttle at least one PTX3 portion into a host or to express at least one PTX3 portion by transcription and/or translation in a host or using at least partially purified components. Activators (e.g., interleukin-6, NF-κB, receptor agonists) or inhibitors (e.g., antibody, IκB,H receptor antagonists) may also be used as agents to modulate PTX3 activity. The agent may be derived from humans or nonhuman animals (e.g., mammals).

The subject may be a female patient or animal. The composition may be suitable for systemic administration or adapted for local administration (i.e., within or around a female reproductive organ). The composition may be used to treat sterility or as a contraceptive.

Another object of the invention is to provide methods of administering the pharmaceutical composition to a subject in need of treatment for female sterility or female contraception in an amount sufficient to increase or decrease, respectively, the subject's reproductive ability.

Detecting PTX3 in a female subject and correlating this amount with her reproductive ability is a further objective of the invention. Mutations in the human PTX3 genetic locus would map to chromosome 3q24–q28; mutations in interacting genes would map outside the PTX3 genetic locus. The function of a PTX3 variant may be determined by comparison to known PTX3 sequences or other pentraxin sequences; folding, glycosylation, secretion, or formation of multimers; receptor binding or signal transduction; effect on reproductive ability, fertility, or sterility; or combinations thereof.

An additional objective of the invention is to screen for at least one agent which changes PTX3 activity, and thereby affects female reproductive ability, as well as to obtain an agent by such processes. Several examples of such agents are disclosed.

Yet another objective of the invention is to provide mammalian cells and nonhuman mammals which are genetically mutated to decrease PTX3 activity. They provide in vitro and in vivo models for defects in reproductive ability (e.g., sterility). They can be used for screening or for trials of potential therapeutics.

Further aspects of the invention will be apparent to a person skilled in the art from the following description and claims, and generalizations thereto.

BRIEF DESCRIPTION OF THE DRAWINGS AND SEQUENCE LISTING

FIGS. 1A–1F illustrate the abnormal morphology of cumuli oophori from PTX3 –/– mice. Cumuli oophori were recovered 14–16 hr after hCG treatment. They are shown after collection (A and B) or 4 hr later (C and D). In PTX3 +/+ mice (A and C), granulosa cells form a compact and stable cumulus around the oocyte (arrow da mettere). In PTX3 –/– mice (B and D), they are loosely associated to the oocyte and the cumulus has completely disappeared in 4 hr. Histological examination of the ovaries of PTX3 +/+ (E) and PTX3 –/– (F) mice shows normal antral follicles.

FIGS. 2A–2D show PTX3 mRNA and protein expression in ovarian tissue. (A) Kinetics of PTX3 expression in ovary after hormonally-induced superovulation (PMS treatment followed 48 hr later by hCG treatment) were shown at the mRNA level. Ovaries were collected at 0, 6, 16, 24 or 48 hr after PMS treatment and then 2, 6, 16, 24 or 48 hr after hCG treatment. Ten µg of total RNA was loaded in each lane. Ethidium bromide staining of the gel is shown in the lower panel. (B) In situ hybridization of the ovary: granulosa cell express PTX3 mRNA only in mature follicles. (C) PTX3 expression by cumuli oophori (C.O.), cumulus oophorus cells (C.O. cells), and oocytes was detected by Western blotting. Cumuli oophori were recovered from four PTX3 +/+ and PTX3 –/– super-ovulated females; cumulus oophorus cells and oocytes were obtained from seven and 14 PTX3 +/+ super-ovulated females, respectively. (D) Phase contrast (right panels) and immuno-fluorescence analysis (left panels) of cumuli oophori from PTX3 –/– (lower panels) and PTX3 +/+ (upper panels) mice are illustrated.

Sequences of a human cDNA and its translated open reading frame (SEQ ID NOS:1–2, respectively), a mouse cDNA and its translated open reading frame (SEQ ID NOS:3–4, respectively), human and mouse upstream regulatory regions (SEQ ID NOS:5–6, respectively), and PCR primers (SEQ ID NOS:7–10) are shown in the Sequence Listing. Alignment of human and mouse amino acid sequences shows 312 of 381 residues are identical (82%) and 351 residues are at least similar (92%). Both genes contain three exons: the first encodes for 43 amino acid residues, the second encodes for 135 amino acid residues with no high similarity to known sequence motifs, and the third encodes 203 amino acid residues with similarity to pentraxins. A pentraxin-like domain includes two Cys residues at positions 162 and 254 and a consensus "pentraxin-like" sequence His-Xaa-Cys-Xaa-Ser/Thr-Trp-Xaa-Ser (SEQ ID NO:11).

DESCRIPTION OF SPECIFIC EMBODIMENTS OF THE INVENTION

Polynucleotides corresponding to all or part of a PTX3 nucleic acid (e.g., transcripts or genes), which include mutants and other variants thereof, may be used to increase PTX3 activity (e.g., in vivo or in vitro expression of PTX3 polypeptide), to supplement or correct a genetic defect (e.g., transfection, infection), to decrease PTX3 activity (e.g., antisense, ribozyme, siRNA), or to detect complementary polynucleotides. Similarly, polypeptides corresponding to a PTX3 protein, which include mutants and other variants thereof, may be used directly to provide PTX3 activity if functional; to produce inhibitory anti-bodies, agonists, and antagonists; and to identify, isolate, or to detect interacting proteins (e.g., antibodies, receptor agonists or antagonists) by binding assays.

Native PTX3 is glycosylated (potential N-linked glycosylation site at position 203). A multimeric PTX3 complex eluted in gel filtration with a relative molecular weight of about 900 kDa. It migrated in gel electrophoresis under nondenaturing and nonreducing conditions as a predominant band of about 440 kDa (e.g., 9- or 10-mer of about 45 kDa protomers) with two minor bands in the 540–600 kDa range. Circular dichroism analysis indicated that PTX3 contained mostly β-sheet structure with some α-helical structure. PTX3 polypeptide or a complex thereof may be identified, isolated, or detected indirectly though a binding molecule (e.g., antibody, natural or nonnatural peptide mimetic) for the PTX3 gene product.

Candidate compounds useful for affecting reproductive ability may interact with a representative PTX3 polynucleotide or polypeptide, and be screened for their ability to provide a method of diagnosis or treatment. These products may be used in assays (e.g., diagnosis) or for treatment; conveniently, they are packaged as assay kits or in pharmaceutical form. Binding to C1q was specific and saturable (one PTX3 protomer bound to one C1q receptor) with a $K_d$ of $7.4 \times 10^{-8}$ M. Kinetic analysis lead to a calculation of $K_{on}$ of $2.6 \times 10^5$ $M^{-1}$ $s^{-1}$ and $K_{off}$ of $4 \times 10^{-4}$ $s^{-1}$. The ligand for C1q binding is the pentraxin-like domain of PTX3 with multimerization being required for binding (possibly through an intramolecular cysteine linkage). Other receptors for PTX3 may be characterized.

Another aspect of the invention is a hybrid PTX3 polynucleotide or polypeptide: e.g., a transcriptional chimera or a translational fusion. In transcriptional chimeras, at least a transcriptional regulatory region of a heterologous gene is ligated to a PTX3 polynucleotide or, alternatively, a transcriptional regulatory region of a PTX3 gene is ligated to at least a heterologous polynucleotide. The reading frames of a PTX3 polypeptide and at least a heterologous amino acid domain are joined in register for a translational fusion. If a reporter or selectable marker is used as the heterologous region or domain, then the effect of mutating PTX3 nucleotide or amino acid sequences on PTX3 function may be readily assayed. In particular, a transcriptional chimera may be used to localize a regulated promoter of a PTX3 gene and a translational fusion may be used to localize PTX3 protein in the cell. For example, transcriptional regulatory regions, ligand-binding domains, or multimerization domains from PTX3 may be involved in a hybrid molecule.

"PTX3" refers to human and mouse genes and proteins, mutants and polymorphisms found in nature, and variant forms thereof (e.g., mutants and analogs not found in nature) as well as analogs thereof. The chemical structure of PTX3 may be a polymer of natural or nonnatural nucleotides connected by natural or nonnatural covalent linkages (i.e., polynucleotide) or a polymer of natural or non-natural amino acids connected by natural or nonnatural covalent linkages (i.e., polypeptide). See Tables 1–4 of WIPO Standard ST.25 (1998) for a nonlimiting list of natural and nonnatural nucleotides and amino acids.

"Mutants" are PTX3 polynucleotides and polypeptides having at least one function that is more active or less active, an existing function that is changed or absent, a novel function that is not naturally present, or combinations thereof. "Polymorphisms" are PTX3 polynucleotides and polypeptides that are genetically changed, but the changes do not necessarily have functional consequences. "Analogs" are PTX3 polynucleotides and polypeptides with different chemical structures, but substantially equivalent function as compared to the native gene or protein. PTX3 functions are described in detail herein. Mutants, polymorphisms, and analogs can be made by genetic engineering or chemical synthesis, but the latter is preferred for nonnatural nucleotides, amino acids, or linkages.

"Oligonucleotides" and "oligopeptides" are short versions of polynucleotides and polypeptides (e.g., less than 30, 60, 90 or 180 nucleotides or amino acids). They may be a fragment of a PTX3 nucleotide or amino acid sequence described herein. Generally, they can be made by chemical synthesis, but cleavage of longer polynucleotides or polypeptides can also be used. Electrophoresis and/or reverse phase high-performance liquid chromatography (HPLC) are suitable biochemical techniques to purify short products.

A PTX3 gene can be identified using stringent hybridization: e.g., 400 mM NaCl, 40 mM PIPES pH 6.4, 1 mM EDTA, 50° C. or 70° C. for an oligonucleotide; 500 mM NaHPO$_4$ pH 7.2, 7% sodium dodecyl sulfate (SDS), 1% bovine serum albumin (BSA), 1 mM EDTA, 45° C. or 65° C. for a polynucleotide of 50 bases or longer. A PTX3 protein can be identified using an antibody or other binding protein as a probe using stringent binding: e.g., 50 mM Tris-HCl pH 7.4, 500 mM NaCl, 0.05% TWEEN 20 surfactant, 1% BSA, room temperature. Washing conditions may be varied by adjusting the salt concentration and temperature such that the signal-to-noise ratio is sufficient for specific hybridization or binding. Such isolation methods may be used to identify an unknown PTX3-related nucleic acid or protein using a probe which detects a known PTX3 nucleic acid or protein, respectively. For example, a mixture of nucleic acids or proteins may be separated by one or more physical, chemical, and/or biological properties, and then the presence or absence of PTX3 nucleic acid or protein may be detected by specific binding of the probe. The probe may also be used to detect the presence or absence of a known PTX3 gene or protein, or to identify a previously unknown PTX3 gene or protein. Blocking and washing conditions can be varied to obtain a nucleic acid hybridization or protein binding signal that is target specific and/or reduces the background.

An "isolated" product is at least partially purified from its cell of origin (e.g., human, other mammal, bacterium, yeast) or manufacturing source. For example, as compared to a lysate of the cell of origin, the isolated product is at least 50%, 75%, 90%, 95% or 98% purified from other chemically-similar solutes (e.g., total nucleic acids for polynucleotides or total proteins for polypeptides). For a chemically-synthesized polymer of nucleotides or amino acids, purity is determined by comparison to prematurely terminated or blocked products and may, as a practical matter, be considered isolated without purification. Purification may be achieved by biochemical techniques such as, for example, cell fractionation, centrifugation, chromatography, electrophoresis, precipitation, specific binding, or combinations thereof. Generally, solvent (e.g., water) and functionally inert chemicals (e.g., salts and buffers) are disregarded when determining purity. Cloning is often used to isolate the desired product. Therefore, a pharmaceutical composition may include agents which are responsible for most if not all of the PTX3 activity.

The meaning of "heterologous" depends on context. For example, ligation of heterologous nucleotide regions to form a chimera means that the regions are not found colinear in nature (e.g., human-derived PTX3 polynucleotide ligated to a human non-PTX3 transcriptional regulatory region). Another example is fusion of amino acid domains which are not found colinear in human (e.g., human-derived PTX3 polypeptide joined to a human non-PTX3 multimerization domain). Ligation of nucleotide regions or joining of amino acid domains, one derived from a human and another derived from an animal, are heterologous because they are derived from different species. In a further example, transfection of a vector or expression construct into a heterologous host cell or transgenesis of a heterologous non-human organism means that the vector or expression construct is not found in the cell's or organism's genome in nature. A "recombinant" product is the result of ligating heterologous regions for a recombinant polynucleotide or fusing heterologous domains for a recombinant polynucleotide. Recombination may be genetically engineered in vitro with purified enzymes or in vivo in a cultured cell.

According to one aspect of invention, polynucleotides (e.g., DNA or RNA, single- or double-stranded) that specifically hybridize to PTX3 genes and transcripts thereof can be used as probes or primers. Such polynucleotides could be full length covering the entire gene or transcribed message (e.g., a recombinant clone in a phagemid, plasmid, bacteriophage, cosmid, yeast artificial chromosome or YAC, bacterial artificial chromosome or BAC, or other vector), an N-terminal "PTX3-unique" or C-terminal "pentraxin-like" domain, an exon or particular coding region, or a shorter length sequence which is unique to PTX3 genes or transcripts thereof but contains only a portion of same. A probe would stably bind its target to produce a hybridization signal specific for a PTX3 polynucleotide or polypeptide, while a primer may bind its target less stably because repetitive cycles of polymerization or ligation will also produce a specific amplification signal. The polynucleotide may be at least 15, 30, 45, 60, 90, 120, 240, 360, 480, 600, 720, 1200, 2400, 5000, 10K, 20K, 40K, 100K, 250K, or 500K nucleotides long (including intermediate ranges thereof).

Typically, a nucleotide sequence may show as little as 85% sequence identity, and more preferably at least 90% sequence identity compared to the coding region of SEQ ID NO: 1 or 3, excluding any deletions or insertions which may be present, and still be considered related. Amino acid sequences are considered to be related with as little as 90% sequence identity compared to SEQ ID NO:2 or 4. But 95% or greater sequence identity is preferred and 98% or greater sequence identity is more preferred.

Use of complex mathematical algorithms is not required if sequences can be aligned without introducing many gaps. But such algorithms are known in the art, and implemented using default parameters in commercial software package. See Doolittle, *Of URFS and ORFS*, University Science Books, 1986; Gribskov and Devereux, *Sequence Analysis Primer*, Stockton Press, 1991; and references cited therein. Percentage identity between a pair of sequences may be calculated by the algorithm implemented in the BESTFIT computer program (Smith and Waterman, J. Mol. Biol., 147:195–197, 1981; Pearson, Genomics, 11:635–650, 1991). Another algorithm that calculates sequence divergence has been adapted for rapid database searching and implemented in the BLAST computer program (Altschul et al., Nucl. Acids Res., 25:3389–3402, 1997).

Conservative amino acid substitutions (e.g., pair Glu/Asp, Val/Ile, Ser/Thr, Arg/Lys or Gln/Asn) may also be considered when making comparisons because the chemical similarity of these pairs of amino acid residues would be expected to result in functional equivalency in many cases. Amino acid substitutions that are expected to conserve the biological function of the polypeptide would conserve chemical attributes of the substituted amino acid residues such as hydrophobicity, hydrophilicity, side-chain charge, or size. Functional equivalency or conservation of biological function may be evaluated by methods for structural determination and bioassay as described herein. Thus, amino acid sequences are considered to be related with as little as 90% sequence similarity between the two polypeptides; however, 95% or greater sequence similarity is preferred and 98% or greater sequence similarity is most preferred.

The codons used in the native nucleotide sequences may be adapted for translation in a heterologous host by adopting the codon preferences of the host. This would accommodate the translational machinery of the heterologous host without a substantial change in the chemical structure of the polypeptide.

PTX3 polypeptide and its variants (i.e., deletion, domain shuffling or duplication, insertion, substitution, or combinations thereof) are also useful for determining structure-function relationships (e.g., alanine scanning, conservative or nonconservative amino acid substitution). For example, folding and processing of PTX3 protein, secretion of PTX3 protomer and formation of multimers, ligand binding to receptor, signal transduction, or combinations thereof. See Wells (Bio/Technology, 13:647–651, 1995) and U.S. Pat. No. 5,534,617. Directed evolution by random mutagenesis or gene shuffling using PTX3 may be used to acquire new and improved functions in accordance with selection criteria. Mutant, polymorphic, and analog PTX3 polypeptides are encoded by suitable mutant, polymorphic, and analog PTX3 polynucleotides. Structure-activity relationships of PTX3 may be studied (i.e., SAR studies) using variant polypeptides produced by an expression construct transfected in a host cell with or without endogenous PTX3. Thus, mutations in discrete domains of the PTX3 polypeptide may be associated with decreasing or even increasing activity in the protein's function.

A PTX3 nucleotide sequence can be used to produce a fusion polypeptide with at least one heterologous peptide domain (e.g., an affinity or epitope tag). Oligopeptide is useful for producing specific antibody and epitope mapping of PTX3-specific antibody. A polypeptide may be at least 10, 15, 20, 25, 30, 35, 40, 45, 50, 60, 70, 80, 90, 100, 150, or more amino acids long (including intermediate ranges thereof). Oligopeptide may be conjugated to one affinity tag of a specific binding pair (e.g., antibody-digoxygenin/hapten/peptide, biotin-avidin/streptavidin, glutathione S transferase-glutathione, maltose binding protein-maltose, protein A or G/immunoglobulin, polyhistidine-nickel). Either a full-length PTX3 polypeptide (e.g., SEQ ID NO:2 or 4) or a shorter fragment (e.g., N-terminal or C-terminal domain) can be produced; optionally including a heterologous peptide domain. PTX3 polypeptide may be synthesized by chemical means, purified from natural sources, synthesized in transfected host cells, or combinations thereof.

The PTX3 nucleotide sequence or a portion thereof can be used to monitor PTX3 expression, to determine PTX3 sequence, and/or to detect PTX3 variants. The invention also provides hybridization probes and amplification primers (e.g., polymerase chain reaction, ligation chain reaction, other isothermal amplification reactions). A pair of such primers may be used for RT-PCR assays to quantitate PTX3 transcript abundance within cells. Amplification primers may be between 15 and 30 nucleotides long (preferably about 25 nucleotides), anneal to either sense or antisense strand (preferably the pair will be complementary to each strand), and terminate at the 3' end anywhere within SEQ ID NOS:1, 3 and 5–6 or their complements. Therefore, this invention will be useful for development and utilization of PTX3 primers and other oligonucleotides to quantitate cognate RNA and DNA within cells.

Binding of polynucleotides or polypeptides may take place in solution or on a substrate. The assay format may or may not require separation of bound from not bound. Detectable signals may be direct or indirect, attached to any part of a bound complex, measured competitively, amplified, or combinations thereof. A blocking or washing step may be interposed to improve sensitivity and/or specificity. Attachment of a polynucleotide or polypeptide, interacting protein, or binding molecule to a substrate before, after, or during binding results in capture of an unattached species. Such immobilization will be stably attached to the substrate under washing conditions. See U.S. Pat. Nos. 5,143,854 and 5,412,087.

Changes in gene expression may be manifested in the cell by affecting transcriptional initiation, transcript stability, translation of transcript into protein product, protein stability, glycoprotein processing, rate of folding or secretion, or combinations thereof. The gene, transcript, or polypeptide can also be assayed by techniques such as in vitro transcription, in vitro translation, Northern hybridization, nucleic acid hybridization, reverse transcription-polymerase chain reaction (RT-PCR), run-on transcription, Southern hybridization, metabolic protein labeling, antibody binding, immunoprecipitation (IP), enzyme linked immunosorbent assay (ELISA), radioimmunoassay (RIA), fluorescent labeling or histochemical staining, microscopy and digital image analysis, and fluorescence activated cell analysis or sorting.

A reporter or selectable marker gene whose product is easily assayed may be used for convenient detection. Reporter genes include, for example, alkaline phosphatase, β-galactosidase (LacZ), chloramphenicol acetyltransferase (CAT), β-glucoronidase (GUS), luciferases (LUC), green and red fluorescent proteins (GFP and RFP, respectively), horseradish peroxidase (HRP), β-lactamase, and derivatives thereof (e.g., blue EBFP, cyan ECFP, yellow-green EYFP, destabilized GFP variants, stabilized GFP variants, or fusion variants sold as LIVING COLORS fluorescent proteins by Clontech). Reporter genes would use cognate substrates that are preferably assayed by a chromogen, fluorescent, or luminescent signal. Alternatively, assay product may be tagged with a heterologous epitope (e.g., FLAG, MYC, SV40 T antigen, glutathione transferase, polyhistidine, maltose binding protein) for which cognate antibodies or affinity resins are available. Examples of drugs for which selectable marker genes, which confer resistance, exist are ampicillin, geneticin/kanamycin/neomycin, hygromycin, puromycin, and tetracycline. A metabolic enzyme (e.g., dihydrofolate reductase, HSV-1 thymidine kinase) may be used as a selectable marker in sensitive host cells or auxotrophs. For example, methotrexate can increase the copy number of a polynucleotide linked to a DHFR selectable marker or gancyclovir can negatively select for a viral thymidine kinase selectable marker.

A polynucleotide may be ligated to a linker oligonucleotide or conjugated to one member of a specific binding pair (e.g., antibody-digoxygenin/hapten/peptide epitope, biotin-avidin/streptavidin, glutathione S transferase or GST-glutathione, lectin-sugar, maltose binding protein-maltose, polyhistidine-nickel, protein A/G-immunoglobulin). The polynucleotide may be conjugated by ligation of a nucleotide sequence encoding the binding member. A polypeptide may be joined to one member of the specific binding pair by producing the fusion encoded by such a ligated or conjugated polynucleotide or, alternatively, by direct chemical linkage to a reactive moiety on the binding member by chemical cross-linking. Such polynucleotides and polypeptides may be used as an affinity reagent to identify, to isolate, and to detect interactions that involve specific binding of a transcript or protein product of the expression vector. Before or after affinity binding of the transcript or protein product, the member attached to the polynucleotide or polypeptide may be bound to its cognate binding member. This can produce a complex in solution or immobilized to a support. A protease recognition site (e.g., for enterokinase, Factor Xa, ICE, secretases, thrombin) may be included between adjoining domains to permit site specific proteolysis that separates those domains and/or inactivates protein activity.

Probes and primers may be used to identify a PTX3 gene or variant thereof. For example, a probe or primer specific for a human PTX3 gene identified herein may be used to detect the presence or absence of the gene, and thereby infer that the source of the gene is present or absent, respectively. Genetic polymorphisms and mutations in the PTX3 gene may be specifically detected by positioning a potentially mismatched base(s) in the middle portion of a probe or the 3'-end of a primer to stabilize or to destabilize binding of the probe or primer to its target depending on whether the target's sequence at that position is complementary to the base or not, respectively.

Genetic polymorphisms and mutations may also be detected by a change in the length of a restriction fragment (RFLP), nuclease-protected fragment (e.g., S1 nuclease, deoxyribonuclease I, ribonuclease A, H or T1), or amplified product. For complicated genetic fingerprints, identification of each component may not be needed because a side-by-side visual comparison might easily detect differences (e.g., RAPD). Differences may also be detected by changes in the molecular weight (MW) or isoelectric point (pI) of the PTX3 protein by gel electrophoresis or isoelectric focusing, respectively.

Presence of PTX3 protein may be used as an indication of PTX3 activity in human or animal fluids or tissues. The fluid may be blood, blood product (e.g., plasma, serum), lavage, sputum, or the like. Exemplary tissues are those of the epithelium (e.g., lung) or mucosa (e.g., mouth, vagina), although infection may be systemic and involve other tissue types as well. Signal may be detected in situ for solid tissue, on dispersed or homogenized tissue, in solution (e.g., diluted or undiluted body fluid, wash), or on a cell smear or touch prep. Oocyes which may be fertilized can be selected by PTX3 expression.

Construction of Shuttle or Expression Vectors

A shuttle or expression vector is a recombinant polynucleotide that is in chemical form either deoxyribonucleic acid (DNA) and/or ribonucleic acid (RNA). The physical form of the vector may be single-stranded or double-stranded; its topology may be linear or circular. The vector is preferably a double-stranded deoxyribonucleic acid (dsDNA) or is converted into a dsDNA after introduction into a cell (e.g., insertion of a retrovirus into a host genome as a provirus). The vector may include one or more regions from a mammalian, insect, plant or fungal gene or a virus (e.g., adenovirus, adeno-associated virus, cytomegalovirus, fowlpox virus, herpes simplex virus, lentivirus, Moloney leukemia virus, mouse mammary tumor virus, Rous sarcoma virus, SV40 virus, vaccinia virus), as well as regions suitable for genetic manipulation (e.g., selectable marker, linker with multiple recognition sites for restriction endonucleases, promoter for in vitro transcription, primer annealing sites for in vitro replication). The vector may be associated with proteins and other nucleic acids in a carrier (e.g., packaged in a viral particle) or condensed with a chemical (e.g., cationic polymer) to target entry into a cell or tissue, such as granulosa cells of mature ovarian follicles. Choice of vector polynucleotides and methods for introducing them into the female reproductive system (e.g., endometrium, ovary) is within the skill in the art.

An expression vector may be further comprised of a regulatory region for gene expression (e.g., promoter, enhancer, silencer, splice donor or acceptor site, polyadenylation signal, cellular localization sequence). Different levels of transcription can be achieved using an agent with a regulatory system which responds to the agent (e.g., tetracycline/tetR or FK506/FKBP). The vector may be further comprised of one or more splice donor and acceptor sites within an expressed region; Kozak consensus sequence upstream of an expressed region for initiation of translation; and downstream of an expressed region, multiple stop codons in the three forward reading frames to ensure termination of translation, one or more mRNA degradation signals, a termination of transcription signal, a polyadenylation signal, and a 3' cleavage signal. For expressed regions that do not contain an intron (e.g., a coding region from a cDNA), a pair of splice donor and acceptor sites may or may not be preferred. It would be useful, however, to include mRNA degradation signal(s) if it is desired to express one or more of the downstream regions only under the inducing condition.

A shuttle vector may be further comprised of an origin of replication (ARS) which allows replication of the vector integrated in the host genome or as an autonomously replicating episome. Centromere and telomere sequences can also be included for the purposes of chromosomal segregation and protecting chromosome ends, respectively. Random or targeted integration into the host genome is more likely to ensure maintenance of the vector but episomes can be maintained by selective pressure or, alternatively, may be preferred for those applications in which the vector is present only transiently.

A vector may be both a shuttle vector and an expression vector.

An expressed region may be derived from any gene of interest, and provided in either orientation with respect to the promoter. The expressed region in the antisense orientation will be useful for making antisense polynucleotide or siRNA. The gene may be derived from the host cell or organism, from the same species thereof, or designed de novo. Fusions with a domain(s) of genes that may share a function with PTX3 can be assayed to define the domain(s) that confers the function or to provide a multifunctional fusion protein. A fusion may also be made with an epitope tag (e.g., GFP, GST, HA, MYC). Some genes produce alternative transcripts, encode subunits that are assembled as homomultimers or heteromultimers, or produce propeptides that are activated by protease cleavage. The expressed region may encode a translational fusion; open reading frames of the regions encoding a polypeptide and at least one heterologous domain may be ligated in register. If a reporter or selectable marker is used as the heterologous domain, then expression of the fusion protein may be readily assayed or localized. The heterologous domain may be an affinity or epitope tag.

Screening of Candidate Compounds

Other aspects of the invention are chemical or genetic compounds, derivatives thereof, and compositions including same that are effective in treatment of sterility or contraception. The amount that is administered to a subject in need of treatment, its formulation, and the timing and route of delivery is effective to reduce fertility, to increase or decrease reproductive ability, or to enhance fertility. Determination of such amounts, formulations, and timing and route of drug delivery is within the skill in the art.

A screening method may comprise administering a candidate compound to an organism or incubating a candidate compound with a cell, and then determining whether or not gene expression is modulated. Such modulation may be an increase or decrease in activity that partially or fully compensates for a change that is associated with or may cause fertility or sterility. Gene expression may be increased or decreased at the level of rate of transcriptional initiation or elongation; stability of transcript; rate of translational initiation or elongation, stability of protein; rate of protein processing, folding, or secretion; proportion of protein in active conformation; formation of multimers; binding to receptor; or combinations thereof. See, for example, U.S. Pat. Nos. 5,071,773 and 5,262,300. High-throughput screening assays are possible (e.g., by using parallel processing and/or robotics).

The screening method may comprise incubating a candidate compound with a cell containing a reporter construct, the reporter construct comprising a transcriptional regulatory region of PTX3 covalently linked in a cis configuration to a downstream gene encoding an assayable product; and measuring production of the assayable product. Either a chimera with an upstream region of the PTX3 gene or a translational fusion in frame with the initiating ATG codon may be used to provide the transcriptional regulatory region. For example, any portion of SEQ ID NO:5 or 6 may be used. A candidate compound which increases production of the assayable product would be identified as an agent that activates gene expression while a candidate compound which decreases production of the assayable product would be identified as an agent that inhibits gene expression. See, for example, U.S. Pat. Nos. 5,849,493 and 5,863,733.

Regulation of PTX3 transcription (e.g., transcriptional regulatory region and cognate transcription factor) has been characterized for mouse and human genes (Altmeyer et al., J. Biol. Chem., 270:25584–25590, 1995; Basile et al., J. Biol. Chem., 272:8172–8178, 1997). PTX3 transcription is specific for certain cell types. Responsiveness of PTX3 transcription to cytokine stimulation appears to be mediated through interaction with NFκB and IκB transcription factors, as well as cell-specific factors.

The screening method may comprise measuring in vitro transcription from a reporter construct in the presence or absence of a candidate compound (the reporter construct comprising a transcription regulatory region) and then determining whether transcription is altered by the presence of the candidate compound. In vitro transcription may be assayed using a cell-free extract, partially purified fractions of the cell, purified transcription factors or RNA polymerase, or combinations thereof. See, for example, U.S. Pat. Nos. 5,453,362; 5,534,410; 5,563,036; 5,637,686; 5,708,158; and 5,710,025.

Techniques for measuring transcriptional or translational activity in vivo are known in the art. For example, a nuclear run-on assay may be employed to measure transcription of a reporter gene. Translation of the reporter gene may be measured by determining the activity of the translation product. The activity of a reporter gene can be measured by determining one or more of transcription of polynucleotide product (e.g., RT-PCR or transcript), translation of polypeptide product (e.g., immunoassay of protein), and biological activity of the reporter protein per se.

A compound that increases or decreases PTX3 gene expression or protein activity could then be assayed for its effect on reproductive ability, reducing fertility, or enhancing fertility.

An epitope-tagged PTX3 protein or antibody specific for PTX3 protein may be used to affinity purify a multimer or other PTX3-containing complex. Candidate compounds may be screened for their ability to decrease the abundance (i.e., steady-state level of complex), rate of assembly, secretion, or biological activity of the complex. For example, a compound that enhances or inhibits binding between PTX3 protein and its receptor may be identified. PTX3 protein can be attached to a substrate as described above. A candidate compound is incubated with the immobilized PTX3 protein in the presence of at least one other component of the complex in at least partially purified form or as a crude mixture. Moreover, one or more components of the complex can be attached to a substrate and a candidate compound can be incubated with the immobilized component in the presence of PTX3 protein with or without additional components of the complex in at least partially purified form or as a crude mixture. Examples of conditions for binding are shown below. After incubation, all non-binding components can be washed away, leaving one or more components of the complex bound to the substrate. Complex formation including PTX3 protein may also take place in solution and then the PTX3-containing complex may be immobilized or not. Reduction is a reversible reaction which disassembles PTX3 multimers. The amount of each component of the complex can then be quantified after washing and separation of the complex from other proteins (e.g., heterogeneous assay) or without separation (e.g., homogeneous assay). For example, it can be determined using an immunological assay, such as ELISA, RIA, or Western blotting. Complex formation may be determined by binding of an antibody to an epitope which is dependent on formation or an epitope which is masked after formation. Complex may be immobilized before or after formation by binding at least one component of the complex to a substrate. Binding of complex to a substrate may be determined without separation by proximity detection, such as SPA or BiaCore. The amount of the one or more bound components of the complex is determined with and without the candidate compound. A desirable compound is one which increases or decreases PTX3 abundance, assembly, secretion, multimer formation, biological activity, or combinations thereof.

Genetic Compounds for Treatment

Activation may be achieved by inducing an expression vector containing an expressed region which encodes a protein with PTX3 activity or upregulates PTX3 activity (e.g., the full-length coding region or functional portions of the PTX3 gene; hypermorphic mutants, homologs, orthologs, or paralogs thereof; acute phase inducers; positive transcription factors acting on the PTX3 gene) or which encodes a protein relieving suppression of PTX3 activity (e.g., at least partially inhibiting expression of a negative regulator of the PTX3 gene). Overexpression of transcription or translation, as well as overexpressing protein function, is a more direct approach to gene activation. Alternatively, the downstream expressed region may direct homologous recombination into a locus in the genome and thereby replace an endogenous transcriptional regulatory region of the gene with an expression cassette or a particular genetic mutation.

An expression vector may be introduced into a host cell or nonhuman animal by a transfection or transgenesis technique using, for example, one or more chemicals (e.g., calcium phosphate, DEAE-dextran, lipids, polymers), biolistics, electroporation, naked DNA technology, microinjection, or viral infection. The introduced expression vector may integrate into the host genome of the cell or animal, or be maintained as an episome. Many neutral and charged lipids, sterols, and other phospholipids to make lipid carriers are known. For example, neutral lipids are dioleoyl phosphatidylcholine (DOPC) and dioleoyl phosphatidyl ethanolamine (DOPE); an anionic lipid is dioleoyl phosphatidyl serine (DOPS); cationic lipids are dioleoyl trimethyl ammonium propane (DOTAP), dioctadecyldiamidoglycyl spermine (DOGS), dioleoyl trimethyl ammonium (DOTMA), and 1,3-dioleoyloxy-2-(6-carboxyspermyl)-propylamide tetraacetate (DOSPER). Dipalmitoyl phosphatidylcholine (DPPC) can be incorporated to improve the efficacy and/or stability of delivery. FUGENE 6, LIPOFECTAMINE, LIPOFECTIN, DMRIE-C, TRANSFECTAM, CELLFECTIN, PFX-1, PFX-2, PFX-3, PFX-4, PFX-5, PFX-6, PFX-7, PFX-8, TRANSFAST, TFX-10, TFX-20, TFX-50, and LIPOTAXI lipids are proprietary formulations. The polymer may be cationic dendrimer, polyamide, polyamidoamine, polyethylene or polypropylene glycol (PEG), polyethylenimine (PEI), polylysine, or combinations thereof; alternatively, polymeric material can be formed into nanoparticle or microparticle. In naked DNA technology, the vector (usually as a plasmid) is delivered to a cell or tissue, where it may or may not become integrated into the host genome, without using chemical transfecting agents (e.g., lipids, polymers) to condense the vector prior to its introduction into the cell or tissue.

An animal, insect, fungal, or bacterial cell may be transfected; transgenesis may be used with a nonhuman animal. A homologous region from a gene can be used to direct integration to a particular genetic locus in the host genome and thereby regulate expression of the gene at that locus (e.g., homologous recombination of a promoterless reporter or selectable marker at the PTX3 genetic locus) or ectopic copies of the PTX3 gene may be inserted. Polypeptide may also be produced in vitro with a cell extract or in vivo with a genetically manipulated cell, The expression vector may be used to replace function of a gene that is down regulated or totally defective, supplement function of a partially defective gene, or compete with activity of the gene. Thus, the cognate gene activity of the host may be neomorphic, hypomorphic, hypermorphic, or normal. Replacement or supplementation of function can be accomplished by the methods discussed above, and the genetically manipulated cell or organism may be selected for high or low expression (e.g., assessing the amount of transcribed or translated product, or the biological function of either product) of the downstream region. Competition between the expressed downstream region and a neomorphic, hypermorphic, or normal gene may be achieved because of the synthetic interactions present in a multimeric protein complex. Alternatively, a negative regulator or a single-chain antibody that inhibits function intracellularly may be encoded by the downstream region of the expression vector. Therefore, at least partial inhibition of PTX3 activity may be achieved by antisense, ribozyme, or RNA interference technology in which the expression vector contains a downstream region corresponding to the unmodified antisense molecule, ribozyme, or siRNA molecule corresponding to a portion of the PTX3 nucleotide sequence.

A compound that increases or decreases PTX3 gene expression or protein activity could then be assayed for its effect on reproductive ability, reducing fertility, or enhancing fertility.

Antisense polynucleotides may act by directly blocking translation by hybridizing to mRNA transcripts or degrading such transcripts of a gene. The antisense molecule may be recombinantly made using at least one functional portion of a gene in the antisense orientation as a region downstream of a promoter in an expression vector. Chemically modified bases or linkages may be used to stabilize the antisense polynucleotide by reducing degradation or increasing half-life in the body (e.g., methyl phosphonates, phosphorothioate, peptide nucleic acids). The sequence of the antisense molecule may be complementary to the translation initiation site (e.g., between −10 and +10 of the target's nucleotide sequence).

Ribozymes catalyze specific cleavage of an RNA transcript or genome. The mechanism of action involves sequence-specific hybridization to complementary cellular or viral RNA, followed by endonucleolytic cleavage. Inhibition may or may not be dependent on ribonuclease H activity. The ribozyme includes one or more sequences complementary to the target RNA as well as catalytic sequences responsible for RNA cleavage (e.g., hammerhead, hairpin, axehead motifs). For example, potential ribozyme cleavage sites within a subject RNA are initially identified by scanning the subject RNA for ribozyme cleavage sites which include the following trinucleotide sequences: GUA, GUU and GUC. Once identified, an oligonucleotide of between about 15 and about 20 ribonucleotides corresponding to the region of the subject RNA containing the cleavage site can be evaluated for predicted structural features, such as secondary structure, that can render candidate oligonucleotide sequences unsuitable. The suitability of candidate sequences can then be evaluated by their ability to hybridize and cleave target RNA. The ribozyme may be recombinantly produced or chemically synthesized.

siRNA refers to double-stranded RNA of at least 20–25 basepairs which mediates RNA interference (RNAi). Duplex siRNA corresponding to a target RNA may be formed by separate transcription of the strands, coupled transcription from a pair of promoters with opposing polarities, or annealing of a single RNA strand having an at least partially self-complementary sequence. Alternatively, duplexed oligoribonucleotides of at least about 21 to about 23 basepairs may be chemically synthesized (e.g., a duplex of 21 ribonucleotides with 3' overhangs of two ribonucleotides) with some substitutions by modified bases being tolerated. Mismatches in the center of the siRNA sequence, however, abolishes interference. The region targeted by RNA interference should be transcribed, preferably as a coding region of the gene. Interference appears to be dependent on cellular factors (e.g., ribonuclease III) that cleave target RNA at sites 21 to 23 bases apart; the position of the cleavage site appears to be defined by the 5' end of the guide siRNA rather than its 3' end. Priming by a small amount of siRNA may trigger interference after amplification by an RNA-dependent RNA polymerase.

Antibody specific for PTX3 can be used for inhibition or detection. Polyclonal or monoclonal antibodies may be prepared by immunizing animals (e.g., chicken, hamster, mouse, rat, rabbit, goat, horse) with antigen, and optionally affinity purified against the same or a related antigen. Antigen may be native protein, fragment made by proteolysis or genetic engineering, fusion protein, or in vitro translated or synthesized protein which includes at least one or more epitopes bound by the antibody. Antibody fragments may be prepared by proteolytic cleavage or genetic engineering; humanized antibody and single-chain antibody may be prepared by transplanting sequences from antigen binding domains of an antibody to framework molecules. Other binding molecules (e.g., agonists or antagonists of ligand-receptor binding) may be prepared by screening a combinatorial library for a member which specifically binds antigen (e.g., phage display library). Antigen may be a full-length protein encoded by the gene or fragment(s) thereof. The antibody may be specific for PTX3 or it may cross react with other pentraxins depending on how well the epitope recognized by the antibody is conserved among different species. See, for example, U.S. Pat. Nos. 5,403,484; 5,723,286; 5,733,743; 5,747,334; and 5,871,974.

PTX3-specific binding agents (e.g., polynucleotides, polypeptides) may be used diagnostically to detect PTX3 nucleic acid or protein, or for treatment to inhibit PTX3 activity (e.g., transcription, translation, processing, secretion, receptor binding). In particular, agents that affect PTX3 transcription and PTX3 binding to a receptor are desirable.

Antibodies or other such PTX3-specific binding agents may be used, for example, in combination with targeting moieties, such as liposomes or other carriers bearing further target specific moieties, such as granulosa cell targeting moieties and/or moeities which target the PTX3-specific binding agents to the extracellular matrix of the cumulous oophorus. Preferably, in this embodiment, the PTX3-binding agent or antagonist is released or otherwise activiated or made to become active after reaching the target, to increase to effectiveness and/or localized action of the binding agent and/or antagonist.

Formulation of Compositions

Compounds of the invention or derivatives thereof may be used as a medicament or used to formulate a pharmaceutical composition with one or more of the utilities disclosed herein.

It is therefore an object of the present invention the use of the recombinant human PTX3 for preparing a medicament for increasing the reproductive ability in a female subject.

A further object of the present invention is the use of virals or plasmids vectors containing the human PTX3 cDNA for the treatment of female subjects in need of increasing reproductive ability.

A further object of the present invention is to provide compounds, compositons and methods to decrease female fertility, such as to provide a contraceptive and contraception method.

Compounds and compositions of the present invention may be used, for example, as antgonists of PTX3 to redeuce and/or eliminate PTX3 actions in, preferably, the extracellular matrix of the cumulous oophorus, and/or to reduce or eliminate the production of PTX3, preferably, the extracellular matrix of the cumulous oophorus, alone or in combination with other contraceptive compounds and/or devices, to reduce female fertility.

A further object of the present invention is the use of PTX3 protein as diagnostic marker of the reproductive ability in human female and/or to confirm the infertility of the human or other mammalian female in which PTX3 expression and action is critical to oocyte fertiliztion.

A further object of the present invention is the use of PTX3 as a target protein for the screening of pharmaceutical compounds to asses their capability to affect the reproductive ability and/or inability in a female subject.

The present invention provides an isolated and/or purified polynucleotide sequence encoding a polypeptide containing an amino acid sequence of SEQ.ID.NOs: 2 or 4, and complements of the polynucleotides, functional fragments of the polynucleotides and functional fragments of the complements of the polynucleotides.

The present invention further provides a polynucleotide containing a nucleotide sequence of SEQ ID NOs: 1, 3, 5 or 6, and complements thereof, as well as RNA equivalents of the noted SEQ ID NOs: and complements thereof wherein T is U.

The present invention provides a monoclonal antibody that binds immunologically to a polypeptide of the invention, or an antigenic fragment thereof.

The present invention provides a polyclonal antisera, antibodies of which bind immunologically to a polypeptide of the present invention, or an antigenic fragment thereof.

The present invention provides an expression vector containing a polynucleotide sequence encoding a polypeptide of the present invention, wherein the polynucleotide is under control of a promoter operable in cells. In one embodiment, the promoter is operable in granulosa cells of mature follicles of a female subject. Such promoters may be alternatively inducible by an externally applied compound.

The present invention provides a host cell, such as a non-human host cell, transformed with an expression vector of the present invention.

The present invention provides a method for producing a polypeptide of the invention containing the steps of: culturing a host cell of the invention under conditions suitable for the expression of the polypeptide; and recovering the polypeptide from the host cell culture.

The present invention provides a composition, such as a pharmaceutical composition, containing a modulator of PTX3 expression dispersed in a pharmaceutically acceptable carrier, diluent or excipient. In one embodiment, the modulator suppresses transcription of a PTX3 gene. In a further embodiment, the modulator suppresses transcription locally in and/or around an area of granulosa cells of mature follicles and/or the extracellular matrix of the cumulous oophorus. In a further embodiment, the modulator of the invention suppresses translation of a PTX3 transcript. In a further embodiment, the modulator suppresses translation of a PTX3 transcript locally in and/or around an area of granulosa cells of mature follicles and/or the extracellular matrix of the cumulous oophorus. In yet a further embodiment, the modulator alters PTX3 RNA stability by increasing PTX3 RNA degradation.

In one embodiment, the modulator enhances transcription of a PTX3 gene. In a further embodiment, the modulator enhances transcription locally in and/or around an area of granulosa cells of mature follicles and/or the extracellular matrix of the cumulous oophorus. In a further embodiment, the modulator of the invention enhances translation of a PTX3 transcript. In a further embodiment, the modulator enhances translation of a PTX3 transcript locally in and/or around an area of granulosa cells of mature follicles and/or the extracellular matrix of the cumulous oophorus. In yet a further embodiment, the modulator alters PTX3 RNA stability by decreasing PTX3 RNA degradation.

The modulator of the present invention is or may contain, in one embodiment, a polypeptide and/or polynucleotide sequence. The polynucleotide sequence of the modulator may be, when present, DNA and/or RNA, and further optionally contain an expression vector, wherein the expression vector contains a promoter and the polynucleotide sequence, operatively linked. The modulator may further be an antibody or active fragment thereof.

The present invention provides a method of identifying compounds that modulate the activity of PTX3 containing the steps of: obtaining an isolated PTX3 polypeptide or functional equivalent thereof; admixing the PTX3 polypeptide or functional equivalent thereof with a candidate compound; and measuring an effect of the candidate compound on the activity of PTX3, such as an activity related to oocyte fertilization.

A method of producing a modulator of PTX3 activity containing the steps of: providing a cell expressing an PTX3 polypeptide contacting the cell with a candidate compound; measuring PTX3 expression; comparing the PTX3 expression in the presence of the candidate compound with the expression of PTX3 expression in the absence of the candidate compound; wherein a difference in the expression of PTX3 in the presence of the candidate compound, as compared with the expression of PTX3 in the absence of the candidate compound, identifies the candidate compound as a modulator of PTX3 expression; and producing the modulator.

The invention provides a contraceptive method containing the step of administering to a fertile female animal an inhibitor of PTX3 activity, in an amount and for a duration which decreases fertility. The inhibitor may be administered in the method of the invention in conjunction with other contraceptive compounds, compositions and/or devices. The inhibitor of the method may be a modulator of the present invention.

A vector of the invention may be a bacterial, viral or mammalian vector. A modulator of the present invention may be antisense PTX3 RNA, which may optionally be an RNA interference of PTX3 RNA.

The present invention further provides a method of enhancing fertility of a female containing administering to the female an effective amount of PTX3 and/or a PTX3 enhancer dispersed in a pharmacologically acceptable carrier, diluent and/or excipient, wherein the amount is capable of enhancing fertility. A measure of enhanced fertility according to the present invention is specifically enhancing the probability of oocyte fertilization in vivo. A PTX3 enhancer according to the present invention may include a modulator as described herein.

The present invention provides a method of diagnosing infertility containing identifying a mutation in a PTX3 polypeptide and/or polynucleotide, which preferably effects the constituent composition of the extracellular matrix of the cumulous oophorus. In one embodiment, the method contains, optionally, amplification of polynucleotides, and hybridization of the polynucleotides to a labeled polynucleotide or other detectable moiety, optionally also including sequencing of a PTX3 polynucleotide.

The compounds of the present invention may be administered in vitro to cells in culture, in vivo to cells in the body, or ex vivo to cells outside of a subject which may then be returned to the body of the same subject or another. The subject is a female of reproductive age; she wants to become pregnant or is at risk for a pregnancy.

In a preferred embodiment, compounds and compositions of the present invention for decreasing female fertility are administered locally to and/or near a reproductive organ, such as through or with the aide of a vaginal suppository, condom, cream, gel or lotion.

Compounds or derivatives thereof may be used to produce a medicament or other pharmaceutical compositions. Use of compositions which further comprise a pharmaceutically acceptable carrier and compositions which further comprise components useful for delivering the composition to a subject are known in the art. Addition of such carriers and other components to the composition of the invention is well within the level of skill in this art.

A pharmaceutical composition may be administered as a formulation which is adapted for direct application to the female reproductive system (e.g., endometrium, ovary) or suitable for passage through the gut or blood circulation. Alternatively, pharmaceutical compositions may be added to the culture medium. In addition to active compound, such compositions may contain pharmaceutically-acceptable carriers and other ingredients known to facilitate administration and/or enhance uptake. The composition may be administered in a single dose or in multiple doses which are administered at different times.

Pharmaceutical compositions may be administered by any known route. By way of example, the composition may be administered by a mucosal, pulmonary, topical, or other localized or systemic route (e.g., enteral and parenteral). In particular, achieving an effective amount of PTX3 activity in or around the reproductive system may be desired. This may involve use of local application, implantation near a reproductive organ, or vaginal suppository. The term "parenteral" includes subcutaneous, intradermal, intramuscular, intravenous, intraarterial, intrathecal, and other injection or infusion techniques, without limitation.

Suitable choices in amounts and timing of doses, formulation, and routes of administration can be made with the goals of achieving a favorable response in the subject (i.e., efficacy), and avoiding undue toxicity or other harm thereto (i.e., safety). Therefore, "effective" refers to such choices that involve routine manipulation of conditions to achieve a desired effect: e.g., affecting reproductive ability, enhancing fertility, or reducing fertility.

A bolus of the formulation administered to a female subject once a day is a convenient dosing schedule. Alternatively, an effective dose may be administered every other day, once a week, or once a month. Dosage levels of active ingredients in a pharmaceutical composition can also be varied so as to achieve a transient or sustained concentration of the compound or derivative thereof in a subject and to result in the desired therapeutic response. But it is also within the skill of the art to start doses at levels lower than required to achieve the desired therapeutic effect and to gradually increase the dosage until the desired effect is achieved.

Dosing may be timed relative to the female subject's reproductive cycle (e.g., menses). As a practical matter, body temperature or hormone levels may be used as surrogates for events like ovulation and menstruation in reproduction.

The amount of compound administered is dependent upon factors such as, for example, bioactivity and bioavailability of the compound (e.g., half-life in the body, stability, and metabolism); chemical properties of the compound (e.g., molecular weight, hydrophobicity, and solubility); route and scheduling of administration; and the like. It will also be understood that the specific dose level to be achieved for any particular subject may depend on a variety of factors, including age, health, medical history, weight, combination with one or more other drugs, and severity of disease.

The term "treatment" refers to, inter alia, reducing or alleviating one or more symptoms of sterility in an affected subject. For a given subject, improvement in a symptom, its worsening, regression, or progression may be determined by an objective or subjective measure. Treatment may also involve combination with other existing modes of treatment and agents (e.g., superovulation). Thus, combination treatment may be practiced.

EXAMPLES

Heterozygous females and males mice genetically modified for the PTX3 gene are normal and fertile. Breeding inter se yielded the predicted number of homozygous null mice at a Mendelian frequency. However, the breeding between homozygous females and males (PTX3 −/−) is completely infertile. Breeding results indicated that homozygous males are normally fertile when mated with wild type (PTX3 +/+) or heterozygous (PTX3 +/−) females, while PTX3 −/− females are always infertile, independently from the male genotype. Mating experiments indicated that there were no differences between PTX3 −/− and PTX3 +/+ females in the frequency of copulation plugs after spontaneous mating during a four days period or after superovulation (Table 1). The number of spontaneously ovulated eggs (Table 1) (average 7 per mouse, n=4, in PTX3 +/− and 7.8 per mouse, n=8, in PTX3 −/− mice) or hormonally induced ovulated eggs (average 35 per mouse, n=9, in PTX3 +/− and 27 per mouse, n=18, in PTX3 −/− mice) was comparable in +/+ and −/− mice. Data are from one representative experiment of four performed. Oocyte and zona pellucida morphology were normal, and the first polar bodies were observed in about 50% of oocytes obtained 16 hr after human chorionic gonadotropin (hCG) treatment from both PTX3 +/+ and PTX3 −/− mice (Table 1). These data indicate that ovulation and oocyte maturation are normal and are not the cause of infertility. In contrast, morphological abnormalities of the cumuli oophori collected from the oviduct of PTX3 −/− mice (FIGS. 1B and 1D) were consistently observed, since the granulosa cells were loosely associated to the oocytes and did not form the corona radiata. PTX3 −/− derived cumuli were unstable in vitro and granulosa cells spontaneously detached from the oocytes in a short time (15–60 min in PTX3 −/− versus several hours in PTX3 +/+ cumuli) after collection (14–16 hr post hCG, or at day 0.5 after natural mating), quickly leading to oocyte denudation.

TABLE 1

Normal mating frequency and ovulation in PTX3 −/− mice

|  | PTX3 +/+ | PTX3 −/− | P value |
| --- | --- | --- | --- |
| Mating frequency Spontaneus (a) |  |  |  |
| 1st day | 4/9 | 2/10 | NS |
| 2nd day | 2/5 | 2/8 | NS |
| 3th day | 2/3 | 2/5 | NS |
| After superovulation | 4/4 | 8/8 | NS |
| Ovulation Spontaneus (b): |  |  |  |
| mice ovulating | 4/4 | 5/5 | NS |
| eggs per mouse | 7 | 7.8 | −# |
| After superovulation: |  |  |  |
| mice ovulating | 5/5 | 6/6 | NS |
| eggs per mouse | 37.8 | 33.3 | — |
| Presence of polar body in ovulated eggs (c) | 53/98 (54%) | 54/109 (49%) | NS — |

(a) Females were housed with males for a four days period and checked daily for the presence of plugs.
(b) Ovulation was analyzed in females with plugs.
(c) The presence of the first polar body was assessed in oocytes recovered 15 hr after HCG treatment.
NS, not significantly different ($p < 0.05$) from control PTX3 +/+ mice by Fischer's exact test.
Numbers refer to pooled samples from PTX3 +/+ or PTX3 −/− mice. A similar lack of difference was observed in four experiments with 5–7 mice.

To understand whether and when pregnancy was interrupted, zygotes and embryos were collected at different time points after mating after spontaneous or hormonally-induced ovulation. No oocytes developing to the two-cell stage in vivo (day 1.5) (Table 2) nor oocytes with two pronuclei (day 0.5) were ever observed, even if viable sperm were found in the oviduct of deficient mice. To further identify the cause(s) of infertility, PTX3 +/+ blastocysts were transferred to PTX3 −/− pseudopregnant females, but normal pregnancy and delivery were observed. This excludes defects in implantation and subsequent processes.

TABLE 2

Fertilization in PTX3 −/− mice

| Fertilization | PTX3 +/+ | PTX3 −/− | P value |
| --- | --- | --- | --- |
| In Vivo Eggs fertilized over total (a) |  |  |  |
| Spontaneus ovulation: | 17/28 (60%) | 0/39 (0%) | <0.0001# |
| After superovulation: | 81/162 (50%) | 0/192 (0%) | <0.0001 |
| In Vitro |  |  |  |
| After zona pellucida removal (b) | 21/27 (77%) | 21/31 (68%) | NS+ |

TABLE 2-continued

Fertilization in PTX3 −/− mice

| Fertilization | PTX3 +/+ | PTX3 −/− | P value |
|---|---|---|---|
| Using intact cumuli oophori (c) | 79/189 (41.8%) | 68/169 (40%) | NS |

(a) Embryos were collected at 1.5 days postcoitum, at the two-cell stage.
(b) Fusion was assessed by the dye transfer technique 4 hr after insemination.
(c) Two cells embryos were counted the day after insemination.
Fischer's exact test.
NS, not significantly different ($p < 0.05$) from control PTX3 +/+ mice.

To evaluate whether PTX3 −/− oocytes could be fertilized, in vitro fertilization (IVF) was performed using wild-type sperm from adult males to inseminate PTX3+/+ or PTX3 −/− oocytes (Table 2). IVF was first conducted with oocytes freed from the zona pellucida and stained with the DNA-specific fluorochrome Hoechst 33258 to observe the fusion. Under these conditions, normal sperm binding to PTX3 −/− oocyte plasma membrane and comparable fusing ability of PTX3 +/+ (77%) and PTX3 −/− (68%) oocytes with sperm (Table 2) were observed. These results suggested that sperm-egg binding and fusion can occur in the absence of PTX3. Intact cumuli collected 13–15 hr after hCG treatment were inseminated and fertilization of PTX3 −/− oocytes and progression to the two-cell stage were observed with a frequency comparable with PTX3 +/+ oocytes (Table 2). These data confirm that oocyte quality is normal in PTX3 deficient mice. Since the cumulus oophorus plays a critical role for in vivo, but not for in vitro fertilization, these results suggest that abnormalities in the cumulus underlie the infertility of PTX3 −/− females.

The expression of PTX3 mRNA in ovarian tissues has been investigated by Northern blotting and in situ hybridization. After hormonally-induced superovulation, PTX3 mRNA expression (assessed by Northern blotting in whole tissue) starts 2 hr after hCG treatment and lasts until 12–14 hr (see FIG. 2A), corresponding to preovulatory expansion until a few hours after ovulation [20]. Granulosa cells obtained by hyaluronidase treatment of cumuli oophori and separation from oocytes expressed PTX3 transcripts.

Expression under normal condition in the absence of superovulation was investigated by in situ hybridization. In situ hybridization of organs from untreated females (FIG. 2B) confirmed the expression of PTX3 mRNA in the ovary, confined to granulosa cells of mature follicles, with no evidence of transcription in oocytes.

Figure 2:
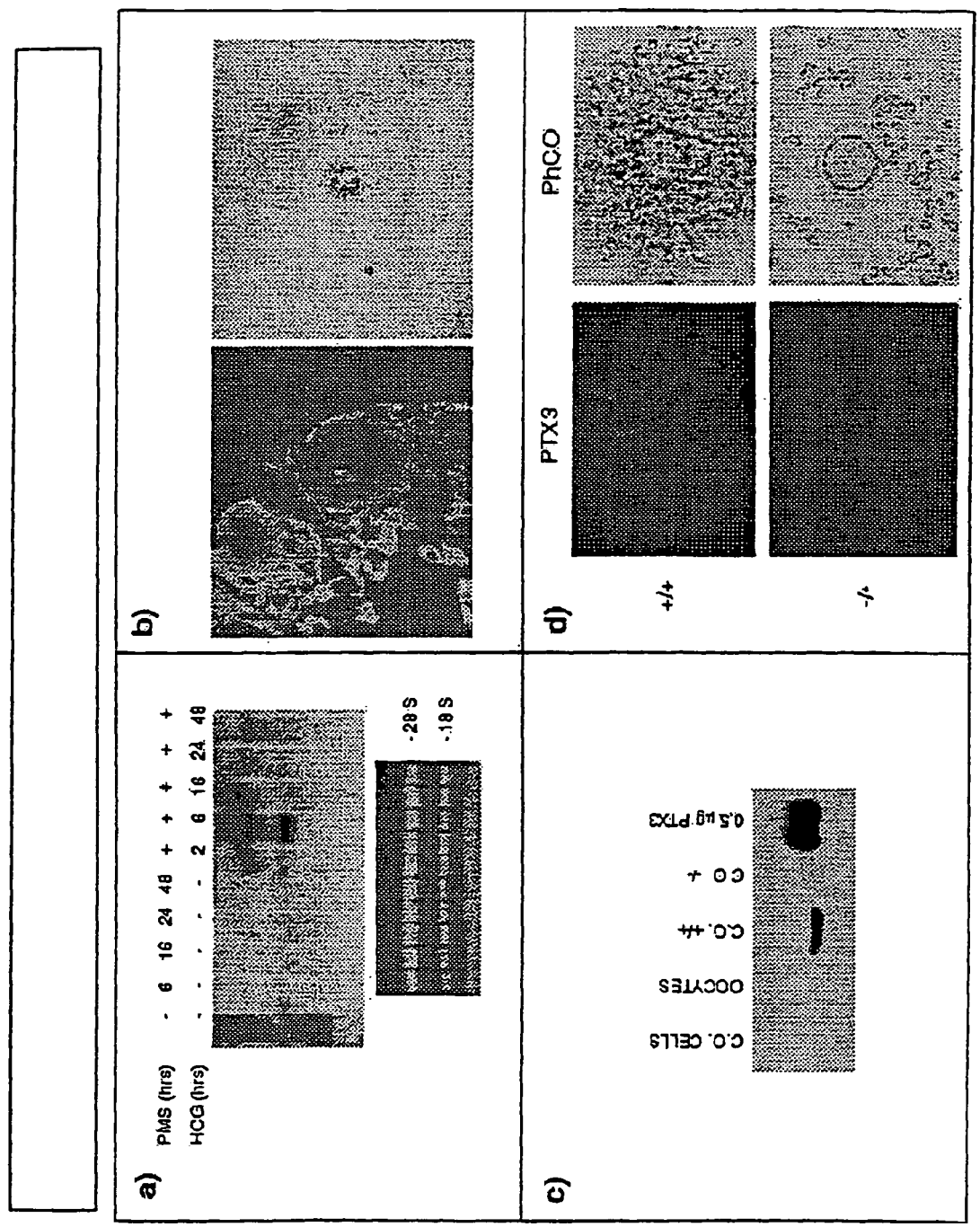

PTX3 protein expression in ovarian tissues was then analyzed. Western blotting indicated that PTX3 was associated with PTX3 +/+ cumuli (in particular with extracellular matrix) because hyaluronidase treatment, which separates cumulus cells from oocytes, abolished immune reactivity (FIG. 2C). Immunofluorescence analysis of PTX3 +/+ and −/− cumuli oophori collected after hormonally-induced superovulation (13–15 hr after hCG) confirmed the association of PTX3 with cumulus intercellular matrix (FIG. 2D).

These data suggest that sterility caused by PTX3 deficiency is due to a lack of oocyte fertilization, as PTX3 deficiency does not affect other steps of reproduction, from mating to ovulation, implantation, and pregnancy. PTX3 transcripts are expressed in the normal ovary exclusively by the granulosa cells of mature follicles, as well as by separated granulosa cells, but not by oocytes. PTX3 mRNA expression is induced in total ovarian tissues following hormonally-induced superovulation. Finally, PTX3 protein has been identified in the extracellular matrix of isolated cumuli, presumably produced by granulosa cells. Analysis of PTX3 −/− mice has identified an abnormal cumulus oophorus as a determinant of infertility. Cumuli oophori from PTX3 −/− females showed morphological abnormalities. They lacked a well-defined corona radiata and, upon in vitro culture, rapidly detached from oocytes. The "fragility" of PTX3 deficient cumuli may reflect a structural role of PTX3 in this peculiar matrix or an alteration in regulatory mechanisms of matrix dissolution. These results identify PTX3 as a novel constituent of the extracellular matrix of the cumulous oophorus, playing a key role in fertility. The cumulus oophorus, though not essential in vitro, plays a key role for in vivo fertilization. Therefore, the abnormalities of the cumulus oophorus are likely to be involved in the infertility of PTX3 −/− female mice.

Varani et al "Knockout of Pentraxin 3, a Downstream Target of Growth Differentiation Factor-9, Causes Female Subfertility", Molecular Endocrinology 16 (6): 1154–1167 (2002), has confirmed many of the results presented herein. Specifically, the authors have reported the induction of PTX3 by growth differentiation factor-9 (GDF-9) in granulosa cells of preovulatory follicles. PTX3 expression in the ovary was observed after the LH surge in the cumulus granulosa cells adjacent to the oocyte and the authors also generated knockout mice lacking the PTX3 gene. The authors have confirmed the present applicants findings that homozygous null (PTX3 −/−) mice develop normally and do not show any gross abnormalities. The authors further confirmed that whereas PTX3 −/− males are fertile, PTX3 −/− females are subfertile due to defects in the integrity of the cumulus cell-oocyte complex.

Varani et al concluded that ovaries and cumulus cell-oocyte complexes within the PTX3 knockout ovaries appear relatively intact before the breakdown of the follicle wall and suggested that PTX3 becomes a part of the mucoelastic extracellular matrix which includes the cumulus cells and oocyte. Varani et al hypothesizes that PTX3 functions to bind to the cumulus cell-oocyte extracellular matrix to protect the oocyte and extracellular matrix from proteolytic enzymes present at the apex of the follicle during the extrusion from the ovary and in the oviductal environment. Varani et al explain that proteolytic degradation of the extracellular matrix is a physiological process that starts after ovulation, leading to progressive oocyte denudation that correlates with a decline in the ability of the oocyte to be fertilized. Proteases produced by the preovulatory follicle and present in the oviductal environment are noted by Varani et al to have been reported to destabilize the cumulus matrix by degrading proteins required for hyaluronan stabilization. Varani et al believe that an untimely release of proteases, as well as a lack of antiprotease activity in the extracellular matrix (e.g. absence of PTX3), might account for early oocyte denudation. Thus, Varani et al confirms that PTX3 appears to protect the cumulus mass that is vital for the capture of the oocyte by the oviductal fimbria and its efficient entry into the oviduct. Varani et al offer an alternative explanation for the decrease in ovulation in the PTX3 −/− knockout mice is that PTX3 on the surface of the cumulus cell-oocyte complex acts to directly bind the complex to the fimbria of the oviduct to shuttle the complex into the oviduct.

Varani et al conclude that the oocytes in PTX3 −/− mice appear to lose their optimal extracellular environment and show a lower efficiency of ovulation and fertilization.

Materials and Methods

Generation of PTX3 −/− Mice

A genomic DNA fragment of 8.5 kb encompassing exons 1 through 2 of the mouse PTX3 gene was used to integrate the IRES-LacZ cassette followed by the PGK-neomycin resistance gene from the pWH9 plasmid in exon 1 at a location 71 bp downstream of the first coding ATG. Methods for the culture, selection, and identification of ES cells were performed as described [20]. Five independently targeted R1 ES cell clones were identified by Southern blot hybridization, using probe A (EcoRI/EcoRV 750 bp fragment in the second intron). No evidence for random integration was detected with the probe B (from the neomycin resistance gene). Two ES cell clones were injected into C57Bl/6 blastocysts. For genotyping of mice, DNA derived from tail biopsies was amplified by polymerase chain reaction with two primers sets (Primer Set 1: 5'-AGCAATGCACCTC-CCTGCGAT-3', SEQ ID NO:7; 5'-TCCTCGGTGGGAT-GAAGTCCA-3' SEQ ID NO:8; Primer Set 2: 5'-CT-GCTCTTTACTGAAGGCTC-3', SEQ ID NO:9; 5'-TCCTCGGTGGGATGAAGT CCA-3, SEQ ID NO:10) that detected the wild type or targeted allele, respectively. Phenotypic analysis was performed on the two lines derived from independent clones, and results were confirmed in a 129Sv-C57Bl/6 mixed and 129Sv inbred genetic background. PTX3 +/+ mice were 129Sv-C57Bl/6 PTX3 −/− littermates, or 129Sv or C57Bl/6 mice obtained from Charles River, Calco, Italy.

Procedures involving animals and their care in conformed with institutional guidelines in compliance with national (4D.L. N.116, G.U., suppl. 40, 18 Feb. 1992) and international law and policies (EEC Council Directive 86/609, OJ L 358,1, 12 Dec. 1987; NIH Guide for the Care and Use of Laboratory Animals, U.S. National Research Council, 1996). All efforts were made to minimize the number of animals used and their suffering.

PTX3 mRNA and Protein

RNA was extracted from cells and purified using TRIZOL reagent (GIBCO BRL). Northern blotting, probe labeling, and hybridization (binding and washing) conditions were performed as described [21].

In situ hybridization: Cryostat sections (13 μm) recovered from wildtype and PTX3 −/− ovaries fixed with paraformaldehyde 4% and frozen in liquid nitrogen were used to perform the in situ hybridization as described [22]. Briefly, slides pemeabilized with proteinase K and 0.2N HCl, were incubated at 65° C. overnight with a radioactively-labelled riboprobe made from PTX3 cDNA containing vector (pBluescript) using a Stratagene RNA transcription kit. Subsequently, specimens were washed with formamide-containing buffer, air dried, dipped in photographic emulsion and incubated at 4° C. in a dark box for at least 10 days. After developing, the slides were counterstained with a solution of 2 μg/ml Hoechst 33258 dye. For Western blot analysis, total cell extracts obtained from intact cumuli oophori, cumulus cells, or oocytes collected from superovulated females were separated by SDS-polyacrylamide gel electrophoresis (Page), electroblotted onto nitrocellulose filters (Hybond ECL, Amersham), and labeled with a purified biotinylated anti-murine PTX3 polyclonal hamster serum (1 μg/ml) followed by streptavidin-HRP (BIOSPA, Italy). Labeled proteins were detected by enhanced chemiluminescence (ECL, Amersham).

Oocyte and Embryo Collection, in vitro Fertilization, and Embryo Transfer

Cumuli oophori, zygotes, and embryos were recovered from the oviduct or uterus of untreated females after natural mating [20]. Superovulation was induced by treatment with 5 units of pregnant mare serum (PMS, Folligon, Intervet) and with 5 units of human chorionic gonadotropin (hCG, Corulon, Intervet) 48 hr later. Cumuli oophori were collected at different time after mating or 13–15 hr after hCG treatment. Cumulus cells and oocytes were separated by hyaluronidase treatment [20].

In vitro fertilization (IVF) of eggs obtained from superovulated females was performed with intact cumuli oophori as described [20] or with zona pellucida free eggs [20] stained with 1 μg/ml Hoechst dye in M16 medium (Sigma) [23] and sperm from BDF males. Fertilization and sperm-egg fusion were assessed by counting two-cell stage embryos the day after insemination of intact cumuli oophori and by counting eggs with fluorescent fertilizing sperm 4 hr after insemination of zona pellucida-free eggs.

Embryo transfer was performed as described [20], using 3.5 day PTX3 +/+ blastocysts implanted in the uterus of 2.5 days pseudopregnant PTX3 −/− females.

REFERENCES

1. Emsley et al., Structure of pentameric human serum amyloid P component. Nature, 1994. 367:338–345.
2. Baumann & Gauldie, The acute phase response. Immunol. Today, 1994. 15:74–80.
3. Steel & Whitehead, The major acute phase reactants: C-reactive protein, serum amyloid P component and serum amyloid A protein. Immunol. Today, 1994. 15:81–88.
4. Breviario et al., Interleukin-1-inducible genes in endothelial cells. Cloning of a new gene related to C-reactive protein and serum amyloid P component. J. Biol. Chem., 1992. 267:22190–22197.
5. Lee et al., TSG-14, a tumor necrosis factor- and IL-1-inducible protein, is a novel member of the pentaxin family of acute phase proteins. J. Immunol., 1993. 150:1804–1812.
6. Lee et al., Relationship of TSG-14 protein to the pentaxin family of major acute phase proteins. J. Immunol., 1994. 153:3700–3707.
7. Vidal Alles et al., Inducible expression of PTX3, a new member of the pentraxin family, in human mononuclear phagocytes. Blood, 1994. 84:3483–3493.
8. Introna et al., Cloning of mouse PTX3, a new member of the pentraxin gene family expressed at extrahepatic sites. Blood, 1996. 87:1862–1872.
9. Bottazzi et al., Multimer formation and ligand recognition by the long pentraxin PTX3—Similarities and differences with the short pentraxins C-reactive protein and serum amyloid P component. J. Biol. Chem., 1997. 272:32817–32823.
10. Muller et al., Circulating levels of the long pentraxin PTX3 correlate with severity of infection in critically ill patients. Crit. Care Med. 2001. 29:1404–1407.
11. Noland et al., The sperm acrosomal matrix contains a novel member of the pentaxin family of calcium-dependent binding proteins. J. Biol. Chem., 1994. 269:32607–32614.
12. Reid & Blobel, Apexin, an acrosomal pentaxin. J. Biol. Chem., 1994. 269:32615–32620.

13. Seery et al., Identification of a novel member of the pentraxin family in *Xenopus laevis*. Proc. R. Soc. Lond. B. Biol. Sci., 1993. 253:263–270.
14. Schlimgen et al., Neuronal pentraxin, a secreted protein with homology to acute phase proteins of the immune system. Neuron, 1995. 14:519–526.
15. Omeis et al., Mouse and human neuronal pentraxin 1 (NPTX1): Conservation, genomic structure, and chromosomal localization. Genomics, 1996. 36:543–545.
16. Hsu & Perin, Human neuronal pentraxin II (NPTX2): Conservation, genomic structure, and chromosomal localization.
Genomics, 1995. 28:220–227.
17. Tsui et al., Narp, a novel member of the pentraxin family, promotes neurite outgrowth and is dinamically regulated by neuronal activity. J. Neurosci., 1996. 15:2463–2478.
18. Dodds et al., Neuronal pentraxin receptor, a novel putative integral membrane pentraxin that interacts with neuronal pentraxin 1 and 2 and taipoxin-associated calcium-binding protein 49. J. Biol. Chem., 1997. 272: 21488–21494.
19. Kirkpatrick et al., Biochemical interactions of the neuronal pentraxins. Neuronal pentraxin (NP) receptor binds to taipoxin and taipoxin-associated calcium-binding protein 49 via NP1 and NP2. J. Biol. Chem., 2000. 275: 17786–17792.
20. Hogan et al., Manipulating the Mouse Embryo. A laboratory manual. 2nd Ed., 1994: Cold Spring Harbor Laboratory Press.
21. Introna et al., Treatment of murine peritoneal macrophages with bacterial lipopolysaccharide alters expression of c-fos and c-myc oncogenes. J. Immunol., 1986. 137: 2711–2715.
22. Biffo & Tolosano, The use of radioactively labelled riboprobes for in situ hybridization: Background and examples of application. Liver, 1992. 12:230–237.
23. Conover & Gwatkin, Pre-loading of mouse oocytes with DNA-specific fluorochrome (Hoechst 33342) permits rapid detection of sperm-oocyte fusion. J. Reprod. Fertil., 1988. 82:681–690.
24. Varani et al "Knockout of Pentraxin 3, a Downstream Target of Growth Differentiation Factor-9, Causes Female Subfertility", Molecular Endocrinology 16 (6): 1154–1167 (2002).

Patents, patent applications, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims.

In contradistinction, the prior art is explicitly excluded from the invention to the extent of specific embodiments that would anticipate the claimed invention or destroy novelty. In certain embodiments, the genus of polynucleotides or polypeptides may be recited in the claims with the proviso that native nucleic acids or proteins are excluded (e.g., having a nucleotide or amino acid sequence which is not given in the sequence listing). For example, the degeneracy of the genetic code may be used to provide a polynucleotide having a nucleotide sequence encoding SEQ ID NO:2, but which is not SEQ ID NO:1. Similarly, a PTX3 polypeptide may be provided that is functionally equivalent but not identical to the mouse and/or human protein (e.g., at least 90% identical) by changing one or more of the amino acid residues of SEQ ID NO:2.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method of increasing the reproductive ability in a female subject comprising increasing the amount or activity of Pentraxin 3 (PTX3) in the cumulous oophorus and/or the extracellular matrix of the cumulous oophorus comprising administering PTX3 to said female subject such that the amount or activity of PTX3 in the cumulous oophorus and/or the extracellular matrix of the cumulous oophorus of said female subject is increased and, wherein the reproductive ability in the female subject is increased.

2. The method of claim 1 wherein said administering comprises local administration.

* * * * *